United States Patent
Kitamura

(10) Patent No.: US 8,743,189 B2
(45) Date of Patent: Jun. 3, 2014

(54) IMAGE PROCESSING APPARATUS, IMAGE PROCESSING METHOD, AND COMPUTER-READABLE RECORDING MEDIUM STORING IMAGE PROCESSING PROGRAM

(75) Inventor: Makoto Kitamura, Tokyo (JP)

(73) Assignee: Olympus Corporation, Tokyo (JP)

( * ) Notice: Subject to any disclaimer, the term of this patent is extended or adjusted under 35 U.S.C. 154(b) by 939 days.

(21) Appl. No.: 12/700,141

(22) Filed: Feb. 4, 2010

(65) Prior Publication Data

US 2010/0208047 A1 Aug. 19, 2010

(30) Foreign Application Priority Data

Feb. 16, 2009 (JP) ................................. 2009-032887

(51) Int. Cl.
*G06K 9/00* (2006.01)
*H04N 7/18* (2006.01)
*A61B 1/04* (2006.01)
*G06T 7/00* (2006.01)

(52) U.S. Cl.
CPC ............... *A61B 1/041* (2013.01); *A61B 1/042* (2013.01); *G06T 7/0012* (2013.01); *G06T 7/0081* (2013.01); *G06T 2207/10024* (2013.01); *G06T 2207/10068* (2013.01); *G06T 2207/20148* (2013.01); *G06T 2207/30028* (2013.01); *G06T 2007/30092* (2013.01); *G06T 2207/30096* (2013.01)
USPC .............. 348/65; 382/128; 382/165; 382/172

(58) Field of Classification Search
CPC ........... G06T 2207/10024; G06T 2207/10068; G06T 2207/20148; G06T 2207/30028; G06T 2207/30092; G06T 2207/30096; G06T 7/0012; G06T 7/0081; A61B 1/041; A61B 1/042
USPC ................. 348/65, E7.085; 382/65, 128, 172
See application file for complete search history.

(56) References Cited

U.S. PATENT DOCUMENTS 7,613,335 B2 * 11/2009 McLennan et al. ........... 382/128
7,953,261 B2    5/2011 Nishimura et al.
(Continued)

FOREIGN PATENT DOCUMENTS

CN   101150977 A   3/2008
CN   101252873 A   8/2008
(Continued)

OTHER PUBLICATIONS

Lau et al. ("Detection of bleeding patterns in WCE video using multiple features"; Proceedings of the 29th Annual International Conference of the IEEE EMBS; CitéInternationale; Lyon, France; Aug. 23-26, 2007; pp. 5601-5604).*

(Continued)

*Primary Examiner* — Behrooz Senfi
*Assistant Examiner* — Maria Vazquez Colon
(74) *Attorney, Agent, or Firm* — Scully, Scott, Murphy & Presser, P.C.

(57) ABSTRACT

An image processing apparatus includes an image acquiring unit that acquires an in-vivo image being a captured image of an inside of a body cavity; a feature-data calculating unit that calculates feature data corresponding to a pixel or an area in the in-vivo image; a body-tissue extracting unit that extracts, as a body tissue, a pixel or an area whose feature data corresponds to a predetermined threshold; a criterion creating unit that creates a criterion for detecting a detecting object based on the feature data of the body tissue; and a detecting unit that detects a body tissue corresponding to the criterion as the detecting object.

19 Claims, 23 Drawing Sheets

(56) References Cited

U.S. PATENT DOCUMENTS

| | | |
|---|---|---|
| 8,002,693 B2 * | 8/2011 | Shigemori et al. ............ 600/101 |
| 2005/0036668 A1 | 2/2005 | McLennan et al. |
| 2009/0005642 A1 | 1/2009 | Shigemori et al. |

FOREIGN PATENT DOCUMENTS

| | | |
|---|---|---|
| JP | 2005-192880 | 7/2005 |
| JP | 2009005020 A | 1/2009 |
| WO | 2006112227 A1 | 10/2006 |

OTHER PUBLICATIONS

Japanese Official Action dated Jun. 4, 2013 received in related application JP 2009-032887 together with an English language translation.

* cited by examiner

| HUE $H_{Nen}$ \ SATURATION $S_{Nen}$ | 0.0 | 0.1 | 0.2 | 0.3 | 0.4 | 0.5 | 0.6 | 0.7 | 0.8 | 0.9 | 1.0 |
|---|---|---|---|---|---|---|---|---|---|---|---|
| 0.0 | 0.80 | 0.78 | 0.76 | 0.74 | 0.72 | 0.70 | 0.68 | 0.66 | 0.64 | 0.62 | 0.60 |
| 0.1 | 0.73 | 0.71 | 0.69 | 0.67 | 0.65 | 0.63 | 0.61 | 0.59 | 0.57 | 0.55 | 0.53 |
| 0.2 | 0.67 | 0.65 | 0.63 | 0.61 | 0.59 | 0.57 | 0.55 | 0.53 | 0.51 | 0.49 | 0.47 |
| 0.3 | 0.62 | 0.60 | 0.58 | 0.56 | 0.54 | 0.52 | 0.50 | 0.48 | 0.46 | 0.44 | 0.42 |
| 0.4 | 0.57 | 0.55 | 0.53 | 0.51 | 0.49 | 0.47 | 0.45 | 0.43 | 0.41 | 0.39 | 0.37 |
| 0.5 | 0.53 | 0.51 | 0.49 | 0.47 | 0.45 | 0.43 | 0.41 | 0.39 | 0.37 | 0.35 | 0.33 |
| 0.6 | 0.50 | 0.48 | 0.46 | 0.44 | 0.42 | 0.40 | 0.38 | 0.36 | 0.34 | 0.32 | 0.30 |
| 0.7 | 0.47 | 0.45 | 0.43 | 0.41 | 0.39 | 0.37 | 0.35 | 0.33 | 0.31 | 0.29 | 0.27 |
| 0.8 | 0.44 | 0.42 | 0.40 | 0.38 | 0.36 | 0.34 | 0.32 | 0.30 | 0.28 | 0.26 | 0.24 |
| 0.9 | 0.42 | 0.40 | 0.38 | 0.36 | 0.34 | 0.32 | 0.30 | 0.28 | 0.26 | 0.24 | 0.22 |
| 1.0 | 0.40 | 0.38 | 0.36 | 0.34 | 0.32 | 0.30 | 0.28 | 0.26 | 0.24 | 0.22 | 0.20 |

| HUE $H_{Nen}$ \ SATURATION $S_{Nen}$ | 0.0 | 0.1 | 0.2 | 0.3 | 0.4 | 0.5 | 0.6 | 0.7 | 0.8 | 0.9 | 1.0 |
|---|---|---|---|---|---|---|---|---|---|---|---|
| 0.0 | 0.40 | 0.39 | 0.38 | 0.37 | 0.36 | 0.35 | 0.34 | 0.33 | 0.32 | 0.31 | 0.30 |
| 0.1 | 0.36 | 0.35 | 0.34 | 0.33 | 0.32 | 0.31 | 0.30 | 0.29 | 0.28 | 0.27 | 0.26 |
| 0.2 | 0.33 | 0.32 | 0.31 | 0.30 | 0.29 | 0.28 | 0.27 | 0.26 | 0.25 | 0.24 | 0.23 |
| 0.3 | 0.31 | 0.30 | 0.29 | 0.28 | 0.27 | 0.26 | 0.25 | 0.24 | 0.23 | 0.22 | 0.21 |
| 0.4 | 0.29 | 0.28 | 0.27 | 0.26 | 0.25 | 0.24 | 0.23 | 0.22 | 0.21 | 0.20 | 0.19 |
| 0.5 | 0.27 | 0.26 | 0.25 | 0.24 | 0.23 | 0.22 | 0.21 | 0.20 | 0.19 | 0.18 | 0.17 |
| 0.6 | 0.25 | 0.24 | 0.23 | 0.22 | 0.21 | 0.20 | 0.19 | 0.18 | 0.17 | 0.16 | 0.15 |
| 0.7 | 0.24 | 0.23 | 0.22 | 0.21 | 0.20 | 0.19 | 0.18 | 0.17 | 0.16 | 0.15 | 0.14 |
| 0.8 | 0.22 | 0.21 | 0.20 | 0.19 | 0.18 | 0.17 | 0.16 | 0.15 | 0.14 | 0.13 | 0.12 |
| 0.9 | 0.21 | 0.20 | 0.19 | 0.18 | 0.17 | 0.16 | 0.15 | 0.14 | 0.13 | 0.12 | 0.11 |
| 1.0 | 0.20 | 0.19 | 0.18 | 0.17 | 0.16 | 0.15 | 0.14 | 0.13 | 0.12 | 0.11 | 0.10 |

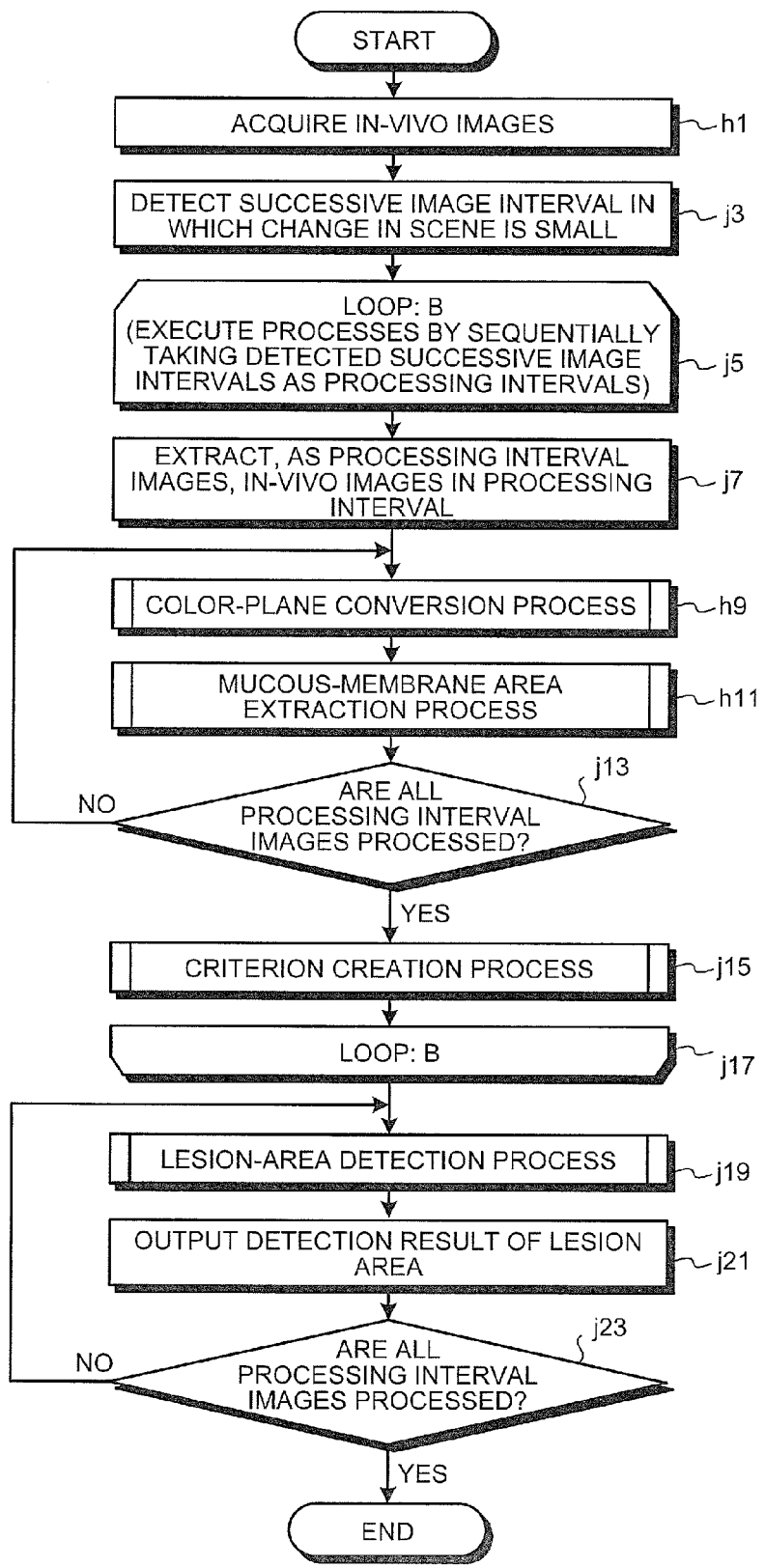

IMAGE PROCESSING APPARATUS, IMAGE PROCESSING METHOD, AND COMPUTER-READABLE RECORDING MEDIUM STORING IMAGE PROCESSING PROGRAM

CROSS-REFERENCE TO RELATED APPLICATIONS

This application is based upon and claims the benefit of priority from Japanese Patent Application No. 2009-032887, filed on Feb. 16, 2009, the entire contents of which are incorporated herein by reference.

BACKGROUND OF THE INVENTION

1. Field of the Invention

The present invention relates to an image processing apparatus, an image processing method, and a computer-readable recording medium storing therein an image processing program for detecting a lesion area from in-vivo images that are captured images of the inside of a body cavity.

2. Description of the Related Art

In recent years, capsule endoscopes have been developed as medical equipments for capturing images of the inside of a body cavity of a subject. The capsule endoscope is swallowed from a mouth, captures images of the inside of a body cavity (in-vivo images) at a predetermined imaging rate while moving through digestive tracts with peristaltic movement or the like, transmits the captured in-vivo images to a receiving device outside the body, and is excreted out of the body in the end. The number of in-vivo images to be captured is approximately represented by the imaging rate (about 2 to 4 frames/sec)×in-vivo residence time of the capsule endoscope (about 8 hours=8×60×60 sec), which results in a large number of images such as more than several tens of thousands of images. Observers such as doctors spend a lot of time to check the large number of in-vivo images transmitted to the receiving device outside the body for identifying a lesion area, by using diagnostic workstations or the like. Therefore, a technology for improving the efficiency of observation operations of the in-vivo images has been strongly desired.

As a technology for solving such a problem, a technology for detecting an abnormality observed area (lesion area) from in-vivo images has been proposed. For example, Japanese Laid-open Patent Publication No. 2005-192880 discloses a technology in which clustering is performed by mapping either a pixel value of each pixel of an in-vivo image or an averaged pixel value to a feature space based on color information, and data whose Euclidean distance from a cluster of a normal mucous-membrane area is equal to or larger than a predetermined value is detected as a lesion area.

SUMMARY OF THE INVENTION

An image processing apparatus according to an aspect of the present invention includes an image acquiring unit that acquires an in-vivo image being a captured image of an inside of a body cavity; a feature-data calculating unit that calculates feature data corresponding to a pixel or an area in the in-vivo image; a body-tissue extracting unit that extracts, as a body tissue, a pixel or an area whose feature data corresponds to a predetermined threshold; a criterion creating unit that creates a criterion for detecting a detecting object based on the feature data of the body tissue; and a detecting unit that detects a body tissue corresponding to the criterion as the detecting object.

An image processing apparatus according to another aspect of the present invention includes an image acquiring unit that acquires a series of in-vivo images being sequentially-captured images of an inside of a body cavity; an image extracting unit that extracts one or more in-vivo images from the series of in-vivo images; a feature-data calculating unit that calculates feature data corresponding to a pixel or an area in the in-vivo images extracted by the image extracting unit; a body-tissue extracting unit that extracts, as a body tissue, a pixel or an area whose feature data corresponds to a predetermined threshold from the in-vivo images extracted by the image extracting unit; a criterion creating unit that creates a criterion for detecting a detecting object based on the feature data of the body tissue; and a detecting unit that detects a body tissue corresponding to the criterion as the detecting object.

An image processing method according to still another aspect of the present invention includes acquiring an in-vivo image being a captured image of an inside of a body cavity; calculating feature data corresponding to a pixel or an area in the in-vivo image; extracting, as a body tissue, a pixel or an area whose feature data corresponds to a predetermined threshold; creating a criterion for detecting a detecting object based on the feature data of the body tissue; and detecting a body tissue corresponding to the criterion as the detecting object.

A computer readable recording medium according to still another aspect of the present invention has stored therein an image processing program including instructions. The instructions cause a computer to execute acquiring an in-vivo image being a captured image of an inside of a body cavity; calculating feature data corresponding to a pixel or an area in the in-vivo image; extracting, as a body tissue, a pixel or an area whose feature data corresponds to a predetermined threshold; creating a criterion for detecting a detecting object based on the feature data of the body tissue; and detecting a body tissue corresponding to the criterion as the detecting object.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 26 is an overall flowchart of a process procedure performed by the image processing apparatus according to the fourth embodiment.

DETAILED DESCRIPTION OF THE PREFERRED EMBODIMENTS

Figure 1:
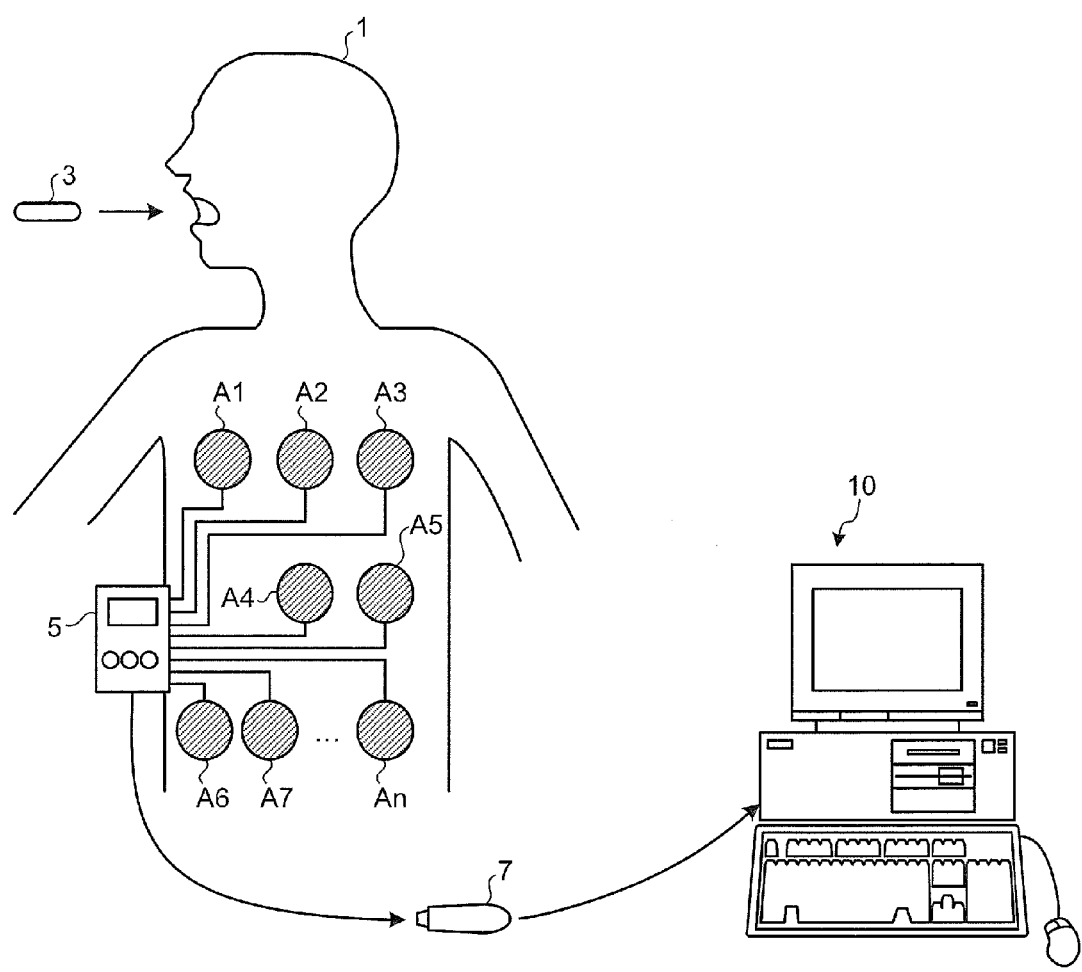
FIG. 1 is a schematic diagram of an overall configuration of an image processing system including an image processing apparatus.

Exemplary embodiments of the present invention are explained in detail below with reference to the accompanying drawings. In the present embodiments, a capsule endoscope that moves through digestive tracts is used as an example of an imaging device, and an image processing apparatus that processes a series of in-vivo images sequentially captured by the capsule endoscope moving through digestive tracts of a subject is described. However, the present invention is not limited by the following embodiments. In the drawings, identical components are denoted by the same reference symbols.

FIG. 1 is a schematic diagram of an overall configuration of an image processing system including an image processing apparatus according to a first embodiment of the present invention. As illustrated in FIG. 1, the image processing system includes a capsule endoscope 3, a receiving device 5, an image processing apparatus 10, and the like. The capsule endoscope 3 captures an image (in-vivo image) of the inside of a subject 1. The receiving device 5 receives the in-vivo image wirelessly transmitted from the capsule endoscope 3. The image processing apparatus 10 processes and displays the in-vivo image captured by the capsule endoscope 3 based on the in-vivo image received by the receiving device 5. For transfer and receipt of image data between the receiving device 5 and the image processing apparatus 10, a field-portable recording medium (portable recording medium) 7 or the like is used.

The capsule endoscope 3 is equipped with an imaging function, a wireless communication function, and the like. The capsule endoscope 3 is introduced into the subject 1 by being swallowed from a mouth of the subject 1, sequentially captures in-vivo images while moving through the inside of digestive tracts, and wirelessly transmits the captured in-vivo images to the outside of the body. The in-vivo images captured by the capsule endoscope 3 are color images having pixel values (RGB values) corresponding to R (red), G (green), and B (blue) color components at respective pixel positions in each image.

The receiving device 5 includes receiving antennas A1 to An that are arranged to be dispersed at positions on the body surface corresponding to a passage route of the capsule endoscope 3 inside the subject 1. The receiving device 5 receives image data wirelessly transmitted from the capsule endoscope 3 via each of the receiving antennas A1 to An. The receiving device 5 is configured to detachably attach the portable recording medium 7 thereto, and sequentially stores received image data in the portable recording medium 7. In this manner, a series of in-vivo images, which are images of the inside of the subject 1 captured by the capsule endoscope 3, are accumulated and stored in the portable recording medium 7 in chronological order by the receiving device 5.

The image processing apparatus 10 is used by a doctor or the like to observe and diagnose the series of in-vivo images captured by the capsule endoscope 3, and is realized by a general-purpose computer such as a workstation or a personal computer. The image processing apparatus 10 is configured to detachably attach the portable recording medium 7 thereto. The image processing apparatus 10 processes the series of in-vivo images stored in the portable recording medium 7, and displays the processed images in chronological order on a display such as an LCD or an EL display.

Figure 2:
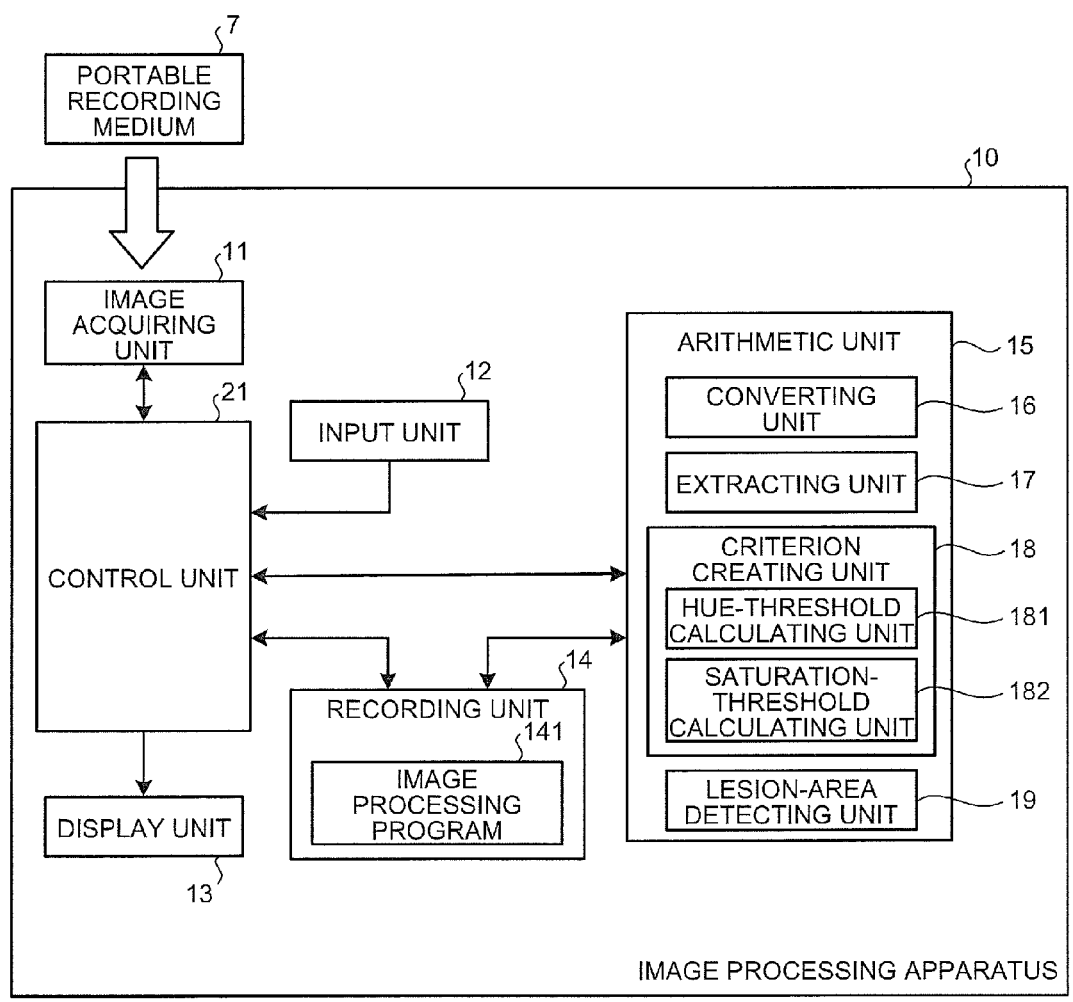
FIG. 2 is a block diagram illustrating a functional configuration of an image processing apparatus according to a first embodiment.

FIG. 2 is a block diagram illustrating a functional configuration of the image processing apparatus 10 according to the first embodiment. In the present embodiment, the image processing apparatus 10 includes an image acquiring unit 11, an input unit 12, a display unit 13, a recording unit 14, an arithmetic unit 15, and a control unit 21 that controls each unit of the apparatus.

The image acquiring unit 11 acquires the series of in-vivo images that are captured by the capsule endoscope 3 and stored in the portable recording medium 7 by the receiving device 5. For example, the image acquiring unit 11 detachably attaches the portable recording medium 7 thereto, and reads to acquire image data of the in-vivo images accumulated in the attached portable recording medium 7. The image acquiring unit 11 is realized by, for example, a read-write device compatible with a type of the portable recording medium 7. Here, acquisition of the series of in-vivo images captured by the capsule endoscope 3 is not limited by use of the portable recording medium 7. For example, it is possible to provide a hard disk instead of the image acquiring unit 11 in the configuration and store the series of in-vivo images captured by the capsule endoscope 3 in advance in the hard disk. It is also possible to separately provide a server instead of the portable recording medium 7 in the configuration and store the time-series images in advance in the server. In this case, the image acquiring unit 11 is constructed of a communication device and the like to enable connection to the server, and the in-vivo images are acquired from the server by connection to the server via the image acquiring unit.

The input unit 12 is realized by, for example, a keyboard, a mouse, a touch panel, and various types of switches, and outputs to the control unit 21 an operational signal corresponding to an operational input. The display unit 13 is realized by a display device such as an LCD or an EL display, and displays various types of screens including a display screen for the in-vivo images with control by the control unit 21.

The recording unit 14 is realized by, for example, a portable recording medium, which includes various types of IC memories such as a ROM as a flash memory being able to update stored data and a RAM, a built-in hard disk, a hard disk connected via a data communication terminal, a readable and writable memory card, and a USB memory; and a reading device for the portable recording medium. The recording unit 14 records therein a computer program for running the image processing apparatus 10 and realizing various functions of the image processing apparatus 10, data to be used during execution of the computer program, and the like. The recording unit 14 also records therein an image processing program 141 for detecting a lesion area in the in-vivo images.

The arithmetic unit 15 is realized by hardware such as a CPU, processes the series of in-vivo images acquired by the image acquiring unit 11, and performs various types of arithmetic processing for detecting a lesion area that appears in each in-vivo image. In the first embodiment, a reddish lesion area having a color property of red, e.g., bleeding or redness, is to be detected. The arithmetic unit 15 includes a converting unit 16, an extracting unit 17 as a body-tissue extracting unit, a criterion creating unit 18, and a lesion-area detecting unit 19 as a detecting unit.

The converting unit 16 uses hue and saturation, which are examples of color elements, as feature data, and converts an in-vivo image into a color plane formed of the hue and the saturation. The extracting unit 17 extracts a mucous-membrane area as an example of a body tissue from an in-vivo image. The criterion creating unit 18 creates a criterion for detecting a lesion area based on the hue and the saturation of the mucous-membrane area extracted by the extracting unit 17. In the first embodiment, the criterion creating unit 18 creates a criterion for detecting a reddish lesion area such as bleeding or redness. The criterion creating unit 18 includes a hue-threshold calculating unit 181 and a saturation-threshold calculating unit 182. The hue-threshold calculating unit 181 calculates a determination threshold in a hue direction based on the hue and the saturation of the mucous-membrane area. The saturation-threshold calculating unit 182 calculates a determination threshold in a saturation direction based on the hue and the saturation of the mucous-membrane area. The lesion-area detecting unit 19 detects a lesion area from an in-vivo image in the color plane converted by the converting unit 16, by using the criterion created by the criterion creating unit 18.

The control unit 21 is realized by hardware such as a CPU. The control unit 21 transfers an instruction, data, and the like to each unit constituting the image processing apparatus 10 based on image data input from the image acquiring unit 11, an operational signal input from the input unit 12, a computer program and data recorded in the recording unit 14, and the like, and centrally controls the overall operations of the image processing apparatus 10.

Figure 3:
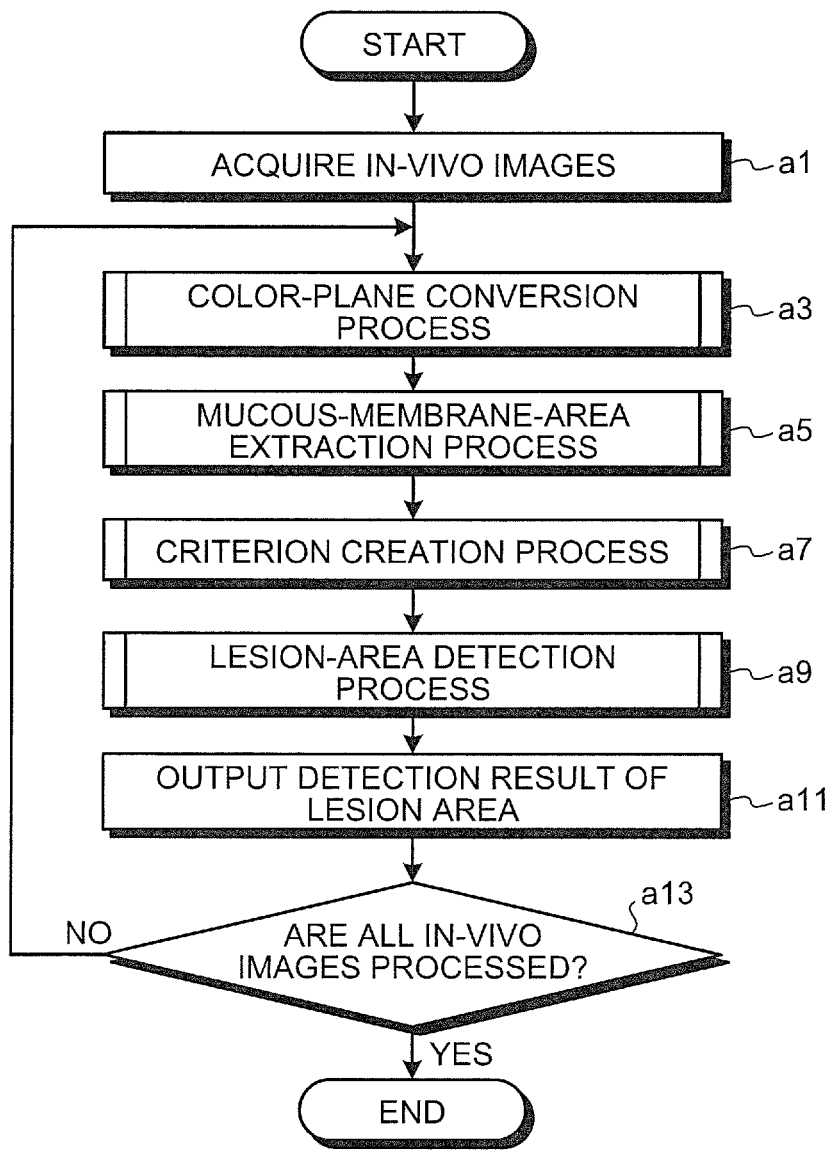
FIG. 3 is an overall flowchart of a process procedure performed by the image processing apparatus according to the first embodiment.

FIG. 3 is an overall flowchart of a process procedure performed by the image processing apparatus 10 according to the first embodiment. The processes described below are realized by causing the arithmetic unit 15 to execute the image processing program 141 recorded in the recording unit 14.

As illustrated in FIG. 3, the arithmetic unit 15 acquires a series of in-vivo images (Step a1). Specifically, the arithmetic unit 15 acquires, via the control unit 21, image data of the series of in-vivo images read out from the portable recording medium 7 by the image acquiring unit 11. Image data of each acquired image is recorded in the recording unit 14 together with an image number indicating a temporal order so that image data of an arbitrary image number can be read out. It is possible to acquire a part of the series of in-vivo images recorded in the portable recording medium 7. In this case, in-vivo images to be acquired can be selected appropriately.

Subsequently, the series of in-vivo images acquired at Step a1 and recorded in the recording unit 14 are sequentially read out one by one. Then, the converting unit 16 performs a color-plane conversion process by taking the read in-vivo image as a processing target (Step a3). Subsequently, the extracting unit 17 performs a mucous-membrane-area extraction process (Step a5), the criterion creating unit 18 performs a criterion creation process (Step a7), and the lesion-area detecting unit 19 performs a lesion-area detection process (Step a9).

Then, the arithmetic unit 15 outputs a detection result of the lesion area with respect to the in-vivo image being the processing target (Step a11). As will be described later, the lesion-area detecting unit 19 generates label data indicating the lesion area. The arithmetic unit 15 displays the lesion area on the display unit 13 via the control unit 21 by creating an image or the like of the lesion area detected from the in-vivo image being the processing target based on the label data.

The arithmetic unit 15 then determines whether the processes from Step a3 to Step a11 are performed by taking all the in-vivo images acquired at Step a1 as the processing targets. When an unprocessed in-vivo image is present (NO at Step a13), the process returns to Step a3 by taking the unprocessed in-vivo image as an in-vivo image being the processing target, and the above-mentioned processes are repeated. On the other hand, when all the in-vivo images are processed (YES at Step a13), the process by the arithmetic unit 15 of the image processing apparatus 10 is terminated.

Although it is explained that the series of in-vivo images consisted of a plurality of in-vivo images are acquired and then a lesion area is detected from each in-vivo image, the number of in-vivo images acquired at Step a1 may be one and a lesion area may be detected from the acquired one in-vivo image.

Figure 4:
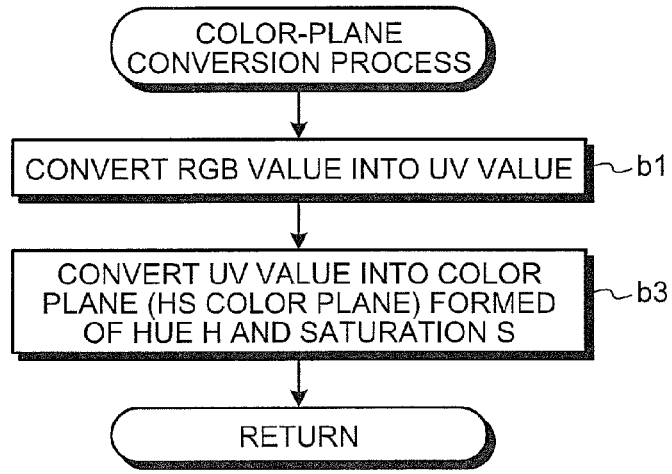
FIG. 4 is a flowchart of a detailed process procedure of a color-plane conversion process.

Next, processes from Step a3 to Step a9 of FIG. 3 are described below in order. Hereinafter, an in-vivo image to be the processing target in each process is referred to as "a processing target image". Firstly, the color-plane conversion process performed by the converting unit 16 at Step a3 of FIG. 3 is described below. FIG. 4 is a flowchart of a detailed process procedure of the color-plane conversion process.

As illustrated in FIG. 4, in the color-plane conversion process, the converting unit 16 converts an RGB value of each pixel constituting the processing target image into a UV value being a color-difference signal (Step b1). The conversion from the RGB value to the UV value is performed according to the following Equations (1) and (2) for example.

$$U = -0.168 \times R - 0.331 \times G + 0.500 \times B \tag{1}$$

$$V = 0.500 \times R - 0.418 \times G + 0.081 \times B \tag{2}$$

As indicated by Equations (1) and (2), the UV value has the following features. That is, the U value is a color-difference signal indicating bluish tone, and the bluish tone is intensified as the U value increases. On the other hand, the V value is a color-difference signal indicating reddish tone, and the reddish tone is intensified as the V value increases.

The capsule endoscope 3 captures a large number of, e.g., more than several tens of thousands of in-vivo images. Therefore, the in-vivo images are generally recorded by being compressed by a compression encoding method such as JPEG or MPEG. In the compression encoding method, a process of converting an RGB value of an image into a YUV value consisted of a luminance signal (Y) and color-difference signals (UV) is performed as an encoding process. Furthermore, in a decoding process for obtaining the RGB value by creating an image of the recorded encoded data, a process opposite to the encoding process is performed such that the YUV value is converted into the RGB value. Therefore, when an in-vivo image compressed by the above-mentioned compression encoding method is handled, the UV value of each pixel obtained through the decoding process may be used in the color-plane conversion process. In this case, because the UV value need not be calculated from the RGB value after creating the image, the process at Step b1 is not necessary. Consequently, whole processing speed can be increased.

Figure 5:
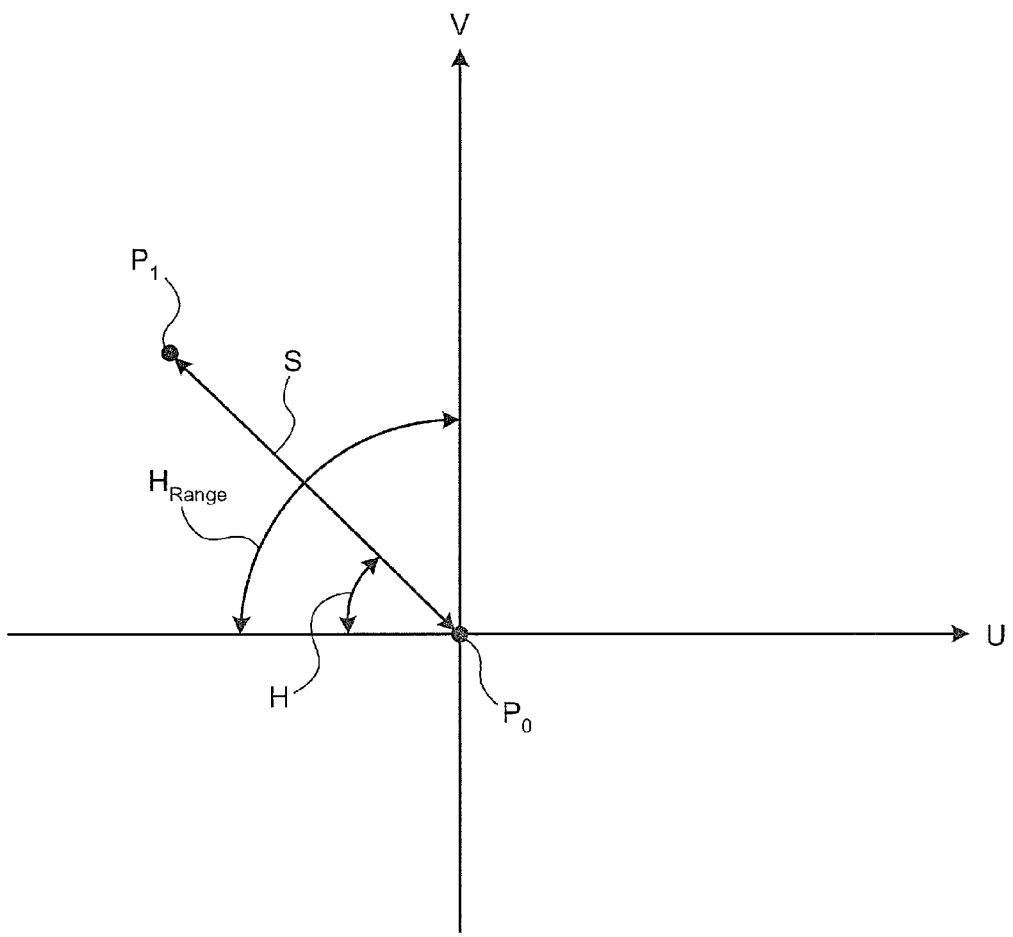
FIG. 5 is a schematic diagram for explaining a principle of calculation of hue and saturation based on UV values.

Subsequently, as illustrated in FIG. 4, the converting unit 16 converts the UV value of each pixel into a color plane formed of hue and saturation (Step b3). Then, the process returns to Step a3 of FIG. 3, and proceeds to Step a5. FIG. 5 is a schematic diagram for explaining a principle of calculation of the hue and the saturation based on the UV value. In FIG. 5, a two-dimensional color plane with the U value on a horizontal axis and the V value on a vertical axis is illustrated. Assuming that one pixel contained in an in-vivo image is paid attention to, and a UV value of this pixel (target pixel) is represented by a point $P_1$, hue of the target pixel corresponds to an angle H between a straight line, which connects an origin $P_0$ of the two-dimensional color plane (UV) and the point $P_1$ determined by the UV value of the target pixel, and the horizontal axis (U). On the other hand, saturation of the target pixel corresponds to a distance S from the origin $P_0$ to the point $P_1$.

In practice, the hue (hereinafter, referred to as "hue H") is calculated according to the following Equation (3) based on the UV value of each pixel.

$$\text{hue } H = a\tan\left(\frac{V}{-U}\right) \quad (3)$$

On the other hand, the saturation (hereinafter, referred to as "saturation S") is calculated according to the following Equation (4) based on the UV value of each pixel.

$$\text{saturation } S = \sqrt{U^2 + V^2} \quad (4)$$

The converting unit 16 calculates respective values of the hue H and the saturation S for each pixel according to Equations (3) and (4) to thereby convert the processing target image into a color plane formed of the hue H and the saturation S (hereinafter, referred to as "an HS color plane" as appropriate).

Here, the method of converting the processing target image into the hue H and the saturation S in units of pixels is described. However, when the conversion is performed in units of pixels, the number of pieces of data to be converted is increased, increasing a processing load. Therefore, it is possible to divide the processing target image into rectangular blocks of a predetermined size, and calculate an average value (average UV value) of UV values of respective pixels constituting each rectangular block per rectangular block. In this case, the calculated average UV value of each rectangular block may be converted into respective values of the hue H and the saturation S. With this configuration, a processing load can be reduced.

It is also possible not to divide the processing target image into the rectangular blocks, but to segment it into areas based on edges, and calculate the average UV value per segmented area. When the area segmentation is performed by taking the edges of the processing target image into consideration as mentioned above, it is possible to improve detection precision of a small lesion area and the like compared to a case where the image is simply divided into the rectangular blocks.

More specifically, an edge detection is performed on a G value, which comparatively represents structural information of an image, or on an image luminance signal (Y), which is calculated according to the following Equation (5), by using a known sobel filter for example. Then, the processing target image is segmented into areas by using a known watershed algorithm (see Luc Vincent and Pierre Soille. Watersheds in digital spaces: An efficient algorithm based on immersion simulations. Transactions on Pattern Analysis and Machine Intelligence, Vol. 13, No. 6, pp. 583 to 598, June 1991.), based on the edge detection result, and an average UV value is calculated per segmented area. Then, the average UV value of each area may be converted into respective values of the hue H and the saturation S.

$$Y = 0.299 \times R + 0.587 \times G + 0.114 \times B \quad (5)$$

Although the method of converting an image into the HS color plane formed of the hue H and the saturation S after converting the image into the UV value is described above, it is possible to convert the image into the HS color plane formed of the hue H and the saturation S by using other color systems. For example, it is possible to obtain an a*b* value from an RGB value according to L*a*b conversion (see CG-ARTS Society, Digital Image Processing, pp. 62 to 63), and covert the image into the HS color plane formed of the hue H and the saturation S by using the a* as the V value and b* as the U value.

It is also possible to directly convert the RGB value into respective values of the hue H and the saturation S by using HSI conversion for example (see CG-ARTS Society, Digital Image Processing, pp. 64 to 68), without calculating the UV value.

Figure 6:
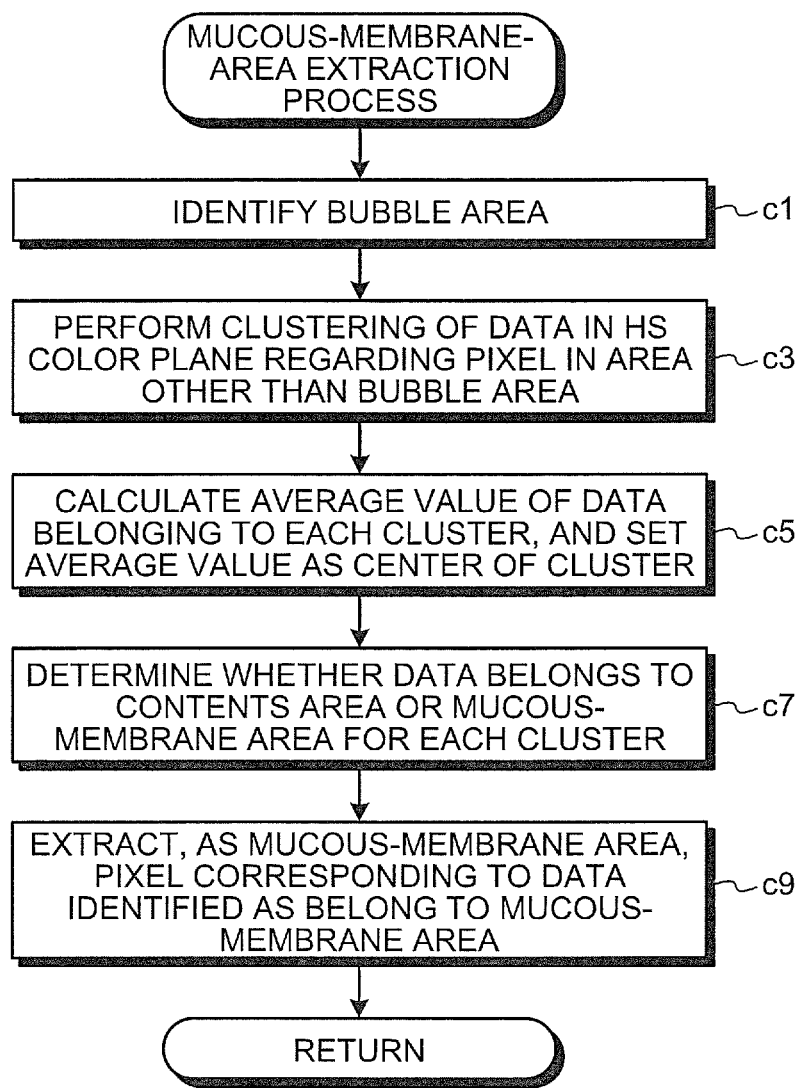
FIG. 6 is a flowchart of a detailed process procedure of a mucous-membrane-area extraction process.

Next, the mucous-membrane-area extraction process performed by the extracting unit 17 at Step a5 of FIG. 3 is described below. In the in-vivo images captured by the capsule endoscope 3, contents such as feces floating inside the body cavity, bubbles, and the like appear in addition to the mucous membrane. In the mucous-membrane-area extraction process, a bubble area and a contents area other than the mucous-membrane area are eliminated and the mucous-membrane area is extracted. FIG. 6 is a flowchart of a detailed process procedure of the mucous-membrane-area extraction process.

As illustrated in FIG. 6, in the mucous-membrane-area extraction process, the extracting unit 17 identifies the bubble area (Step c1). The bubble area can be identified by using a known technique disclosed in Japanese Laid-open Patent Publication No. 2007-313119 for example. Regarding its procedure, an edge intensity of a pixel is calculated based on a G value of the processing target image. Then, a correlation value between the calculated edge intensity and a bubble model set in advance based on the feature of the bubble is calculated, and a portion highly correlated with the bubble model is detected as the bubble area. The applicable technique is not limited to the above, and any methods of identifying the bubble area may be applied appropriately.

Subsequently, the extracting unit 17 performs, as a distribution forming unit, clustering of data in the HS color plane regarding a pixel identified as not corresponding to the bubble area in the processing target image at Step c1 (Step c3). The clustering is a method of dividing a data distribution within a feature space into blocks called clusters based on similarity between pieces of data. For example, the clustering is performed on data in the HS color plane regarding the pixel identified as not corresponding to the bubble area in the processing target image, by using a known method such as a K-means method (see CG-ARTS Society, Digital Image Processing, pp. 232). In this case, a distance between pieces of data in the HS color plane corresponds to the similarity.

In the K-means method, cluster numbers K by which pieces of data are divided needs to be specified in advance as a parameter, and the precision of the clustering greatly varies depending on the specified cluster numbers K. Therefore, to obtain a highly precise clustering result, it is necessary to determine the optimal cluster numbers K for each pixel. In this example, it is assumed that an algorithm for determining the optimal cluster numbers K based on a cluster-numbers evaluation value is used as a method of determining the optimal cluster numbers K (see Chong-Wah Ngo et al, "On Clustering and Retrieval of Video Shots Through Temporal Slices Analysis", Trans Mlt, Vol. 4, No. 4, pp. 446-458, 2002). However, an applicable clustering method is not limited to the K-means method, and other clustering methods may be employed.

Subsequently, as illustrated in FIG. 6, the extracting unit 17 calculates an average value of pieces of data belonging to each cluster based on a result of the clustering, and sets the calculated average value as the center of a corresponding cluster ($H_i$, $S_i$) (Step c5). Here, i=1, ..., K, and K represents the cluster numbers.

Then, the extracting unit 17 determines whether data belongs to the contents area or the mucous-membrane area for each cluster (Step c7). The extracting unit 17 then extracts, as the mucous-membrane area, pixels corresponding to data determined as belonging to the mucous-membrane area (Step c9). Then, the process returns to Step a5 of FIG. 3, and proceeds to Step a7.

Colors of the mucous membrane and the contents are based on absorption properties of blood and bile, respectively, and their absorption wavelengths appear disproportionately on a short wavelength side. Therefore, it is possible to presume that data belonging to the mucous-membrane area and the contents area is distributed in a hue range $H_{Range}$ from red to yellow as illustrated in FIG. 5.

Figure 7:
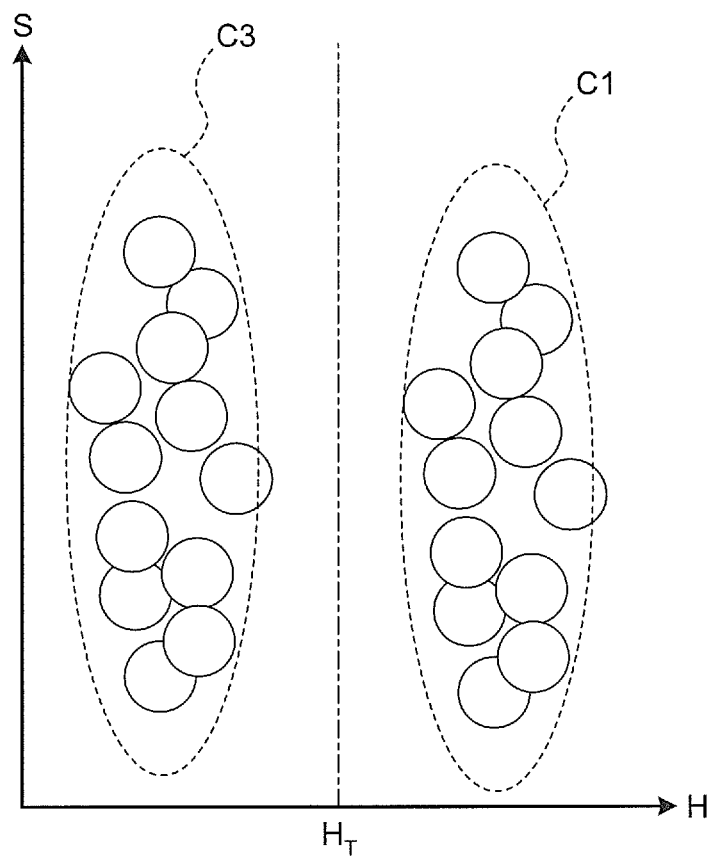
FIG. 7 is a schematic diagram illustrating an example of a distribution of data belonging to a mucous-membrane area and a contents area in a hue range HRange illustrated in FIG. 5.

FIG. 7 is a schematic diagram illustrating an example of a distribution of data belonging to the mucous-membrane area and the contents area in the hue range $H_{Range}$ illustrated in FIG. 5. An RGB-value ratio greatly differs between the mucous-membrane area and the contents area. This is because while the absorption wavelength of hemoglobin, which is a constituent component of the blood present in the mucous membrane, appears in a band ranging from a middle wavelength to a short wavelength by which a G value and a B value are formed, the absorption wavelength of bilirubin, which is a pigment composition of the bile in the contents area such as feces, appears in a short wavelength band by which a B value is formed. Therefore, in most cases, the mucous-membrane area appears in reddish color with the R value comparatively larger than the G value and the B value, and the contents area appears in yellowish color with the R value and the G value comparatively larger than the B value. This causes a difference in the hue H, so that data C1 belonging to the mucous-membrane area and data C3 belonging to the contents area are separated from each other in terms of the hue H as indicated by rounded dashed lines in FIG. 7. Therefore, a determination threshold $H_T$ indicated by a chain line in FIG. 7 is set in advance to distinguish between the data C1 belonging to the mucous-membrane area and the data C3 belonging to the contents area. Accordingly, the extracting unit 17 performs threshold processing on the center $H_i$ of each cluster calculated at Step c5 by the threshold $H_T$. When $H_T<H_i$, the extracting unit 17 determines that data belonging to this cluster is data belonging to the mucous-membrane area. On the other hand, when $H_T \geq H_i$, the extracting unit 17 determines that data belonging to this cluster is data belonging to the contents area.

Figure 8:
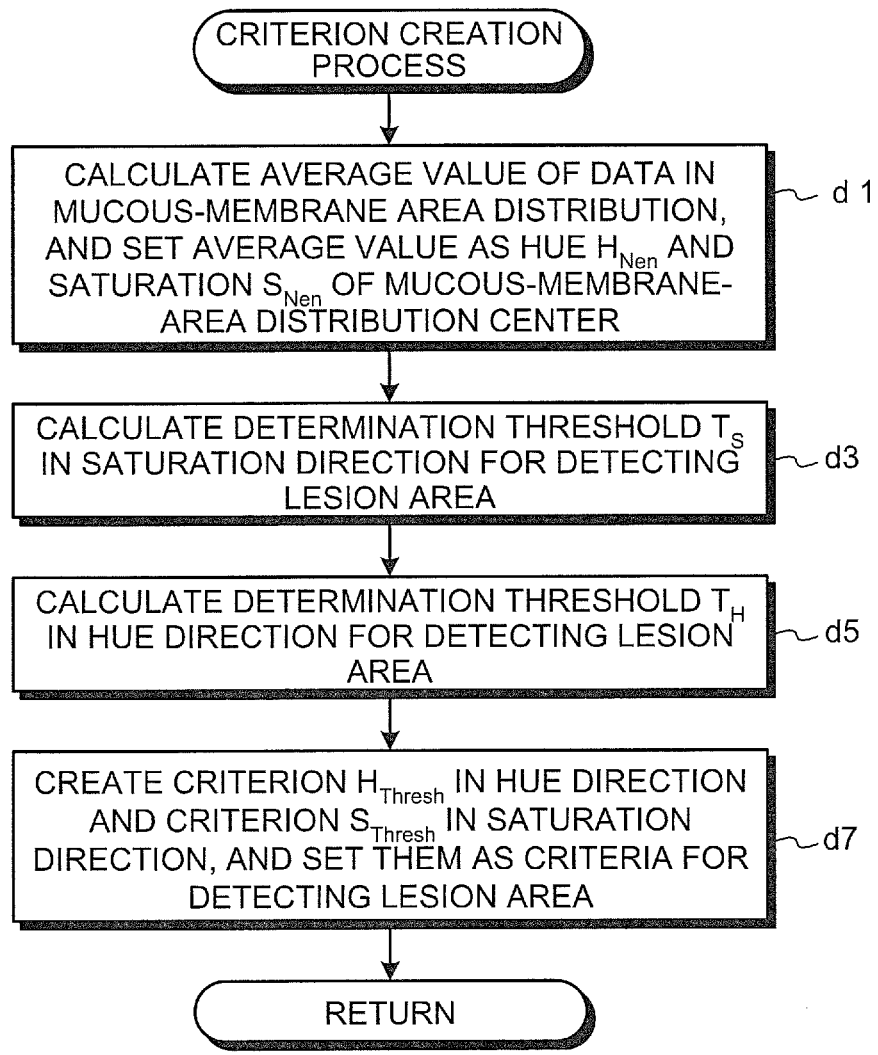
FIG. 8 is a flowchart of a detailed process procedure of a criterion creation process according to the first embodiment.

Next, the criterion creation process performed by the criterion creating unit 18 at Step a7 of FIG. 3 is described below. In the criterion creation process, a criterion is created to determine in which direction and to what extent data should deviate from the center of the HS color plane so as to be determined as belonging to the lesion area, based on the center of a data distribution of the pixels extracted as the mucous-membrane area (hereinafter, referred to as "a mucous-membrane area distribution") in the HS color plane. FIG. 8 is a flowchart of a detailed process procedure of the criterion creation process according to the first embodiment.

As illustrated in FIG. 8, in the criterion creation process, the criterion creating unit 18 calculates an average value of data determined as belonging to the mucous-membrane area distribution at Step c9 of FIG. 6, and sets the calculated average value as hue $H_{Nen}$ and saturation $S_{Nen}$ of the center of the mucous-membrane area distribution (mucous-membrane-area distribution center) (Step d1).

Subsequently, the saturation-threshold calculating unit 182 of the criterion creating unit 18 calculates a determination threshold $T_S$ in a saturation direction (direction of the saturation S) for detecting the lesion area (Step d3). Then, the hue-threshold calculating unit 181 calculates a determination threshold $T_H$ in a hue direction (direction of the hue H) for detecting the lesion area (Step d5). As described above, the mucous-membrane area that actually appears in the in-vivo image may be a mucous-membrane area colored in yellowish color, such as mucous membrane of a small intestine or mucous membrane of a large intestine, or a mucous-membrane area colored in reddish color, such as mucous membrane of a stomach. In the first embodiment, the lesion area to be detected is a lesion area in reddish color. Therefore, each determination threshold is calculated so that a determination threshold in the hue direction and a determination threshold in the saturation direction for the reddish mucous-membrane area, which is similar to a color property of the lesion area, are respectively made smaller than a determination threshold in the hue direction and a determination threshold in the saturation direction for the yellowish mucous-membrane area.

Figure 9:
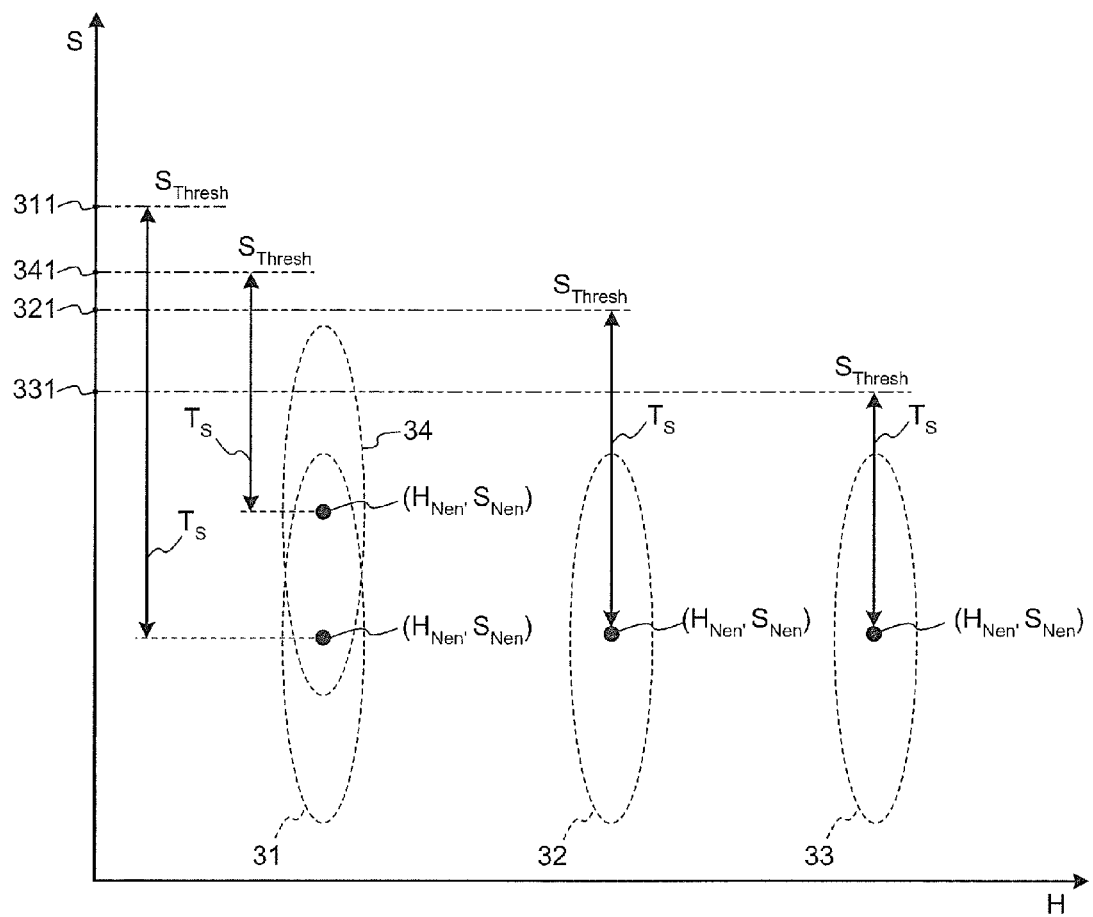
FIG. 9 is an explanatory diagram for explaining a principle of calculation of determination thresholds in a saturation direction.

FIG. 9 is an explanatory diagram for explaining a principle of calculation of the determination thresholds $T_S$ in the saturation direction. Here, it is assumed that there are pieces of data whose hue H deviates in the saturation direction with respect to the yellowish mucous-membrane area distribution. In this case, these pieces of data are highly likely to correspond to a normal mucous membrane that appears in yellow in the image captured via digestive fluid such as the bile. This is because, when the hue H corresponds to yellowish color, even if it deviates in the hue direction, it does not come closer to the property of the reddish lesion area. On the other hand, assuming that there are pieces of data whose hue H deviates in the saturation direction with respect to the reddish mucous-membrane area distribution, these pieces of data are highly likely to correspond to the reddish lesion area.

Therefore, the determination threshold $T_S$ in the saturation direction is calculated so that its value is decreased as the hue $H_{Nen}$ of the mucous-membrane-area distribution center is increased, i.e., as the mucous-membrane area distribution comes closer to reddish color. Namely, by decreasing the determination threshold $T_S$ to be applied to the reddish mucous-membrane area distribution, a detection sensitivity is increased. On the other hand, regarding the yellowish mucous-membrane area distribution, the determination threshold $T_S$ to be applied is increased to prevent error detection. For example, as illustrated in FIG. 9, a determination threshold $T_S$ for a mucous-membrane area distribution 32 is calculated so that it becomes smaller than a determination threshold $T_S$ for a mucous-membrane area distribution 31 whose hue $H_{Nen}$ is smaller than that of the mucous-membrane area distribution 32. Furthermore, a determination threshold $T_S$ for a mucous-membrane area distribution 33 is calculated so that it becomes smaller than the determination threshold $T_S$ for the mucous-membrane area distribution 32 whose hue $H_{Nen}$ is smaller than that of the mucous-membrane area distribution 33.

Furthermore, it is assumed that there are pieces of data whose saturation S deviates in the saturation direction with respect to the reddish mucous-membrane area distribution. In this case, as the saturation S is increased, data is more likely to correspond to a red lesion even with relatively slight deviation in the saturation direction. Therefore, the determination threshold $T_S$ in the saturation direction is calculated so that its value is decreased as the saturation $S_{Nen}$ of the mucous-membrane-area distribution center is increased. For example, as illustrated in FIG. 9, a determination threshold $T_S$ for a mucous-membrane area distribution 34 is calculated so that it becomes smaller than the determination threshold $T_S$ for the mucous-membrane area distribution 31 whose saturation $S_{Nen}$ is smaller than that of the mucous-membrane area distribution 34.

Figure 10:
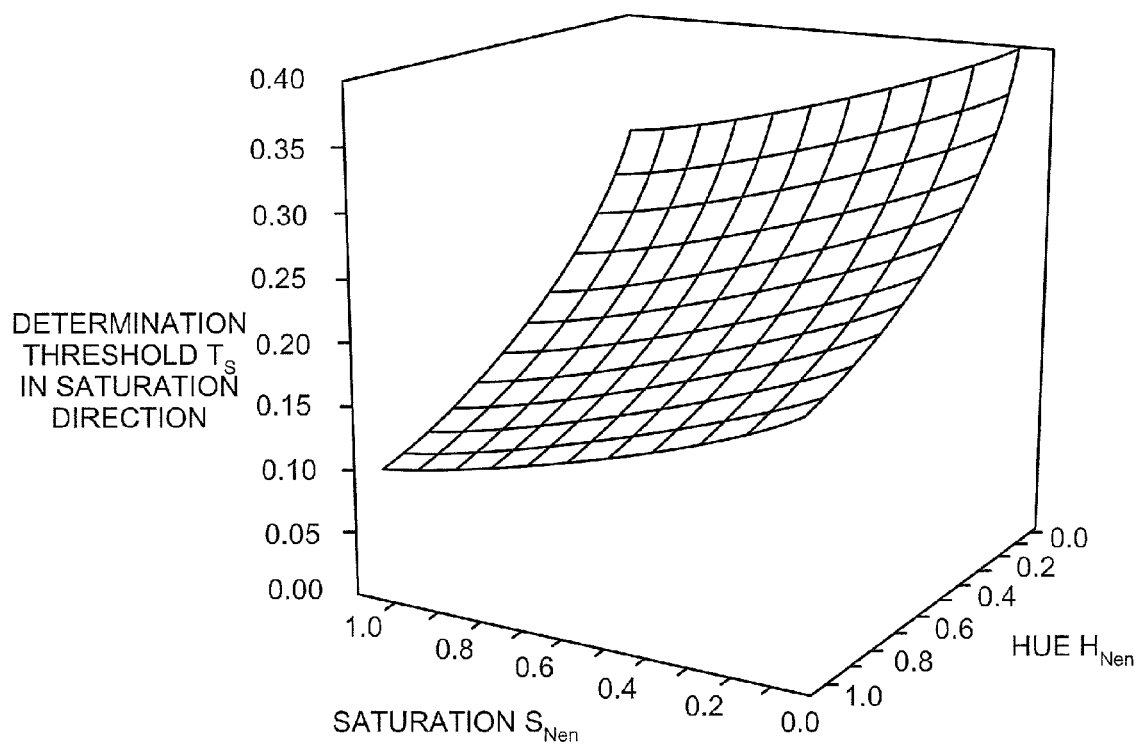
FIG. 10 is a graph of exemplary data of the calculated determination thresholds in the saturation direction.

A calculation formula for the determination threshold $T_S$ in the saturation direction is represented by the following Equation (6). As represented by the following Equation (6), the calculation formula for the determination threshold $T_S$ in the saturation direction is represented by a decreasing function with, for example, the hue $H_{Nen}$ and the saturation $S_{Nen}$ of the mucous-membrane-area distribution center and predetermined coefficients $T_{h1}$ and $T_{s1}$ set in advance. Therefore, the determination threshold $T_S$ in the saturation direction is calculated so that it is decreased as the hue $H_{Nen}$ of the mucous-membrane-area distribution center is increased and it is decreased as the saturation $S_{Nen}$ of the mucous-membrane-area distribution center is increased. FIG. 10 is a graph of exemplary data of the saturation $S_{Nen}$ of the mucous-membrane-area distribution center versus the determination threshold $T_S$ in the saturation direction actually calculated by the following Equation (6) based on the saturation $S_{Nen}$.

$$T_S = (1/(H_{Nen}+1)) \times T_{h1} - S_{Nen} \times T_{s1} \qquad (6)$$

Figure 11:
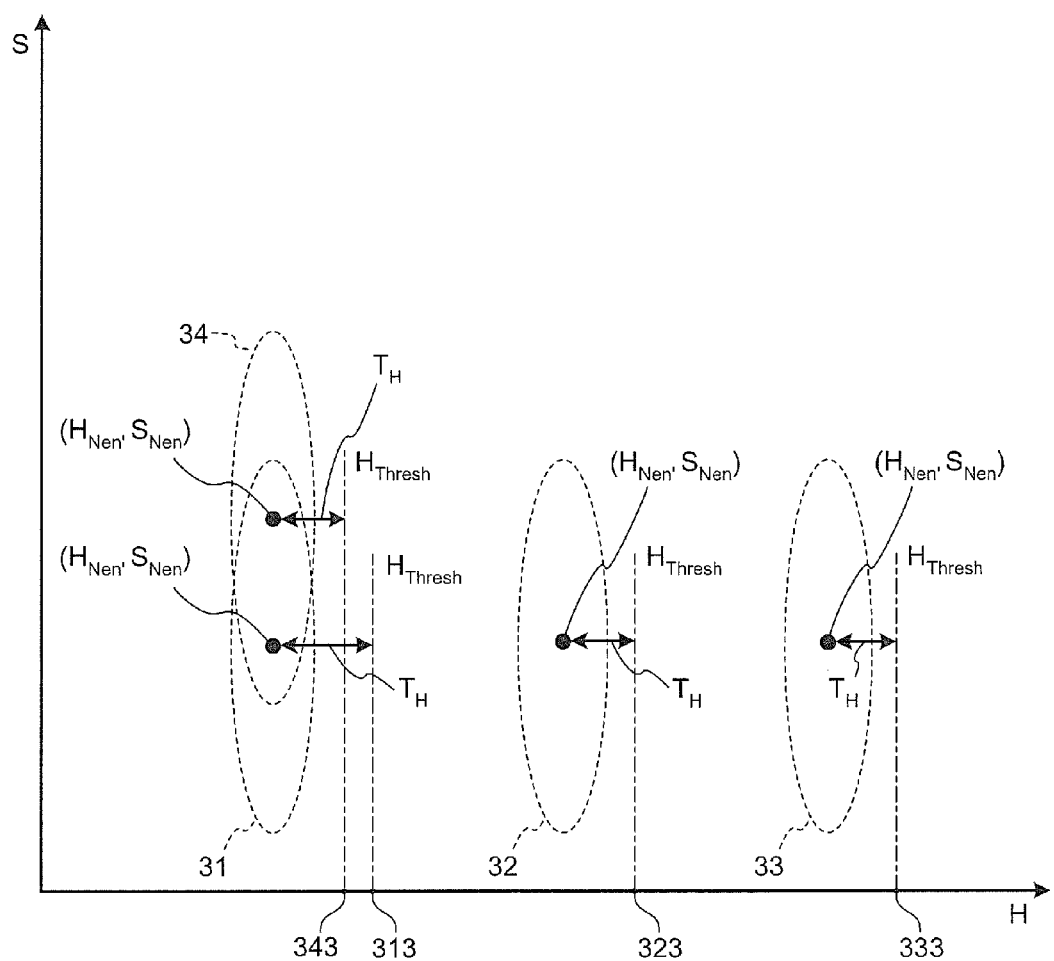
FIG. 11 is an explanatory diagram for explaining a principle of calculation of determination thresholds in a hue direction.

FIG. 11 is an explanatory diagram for explaining a principle of calculation of the determination thresholds $T_H$ in the hue direction, in which the four mucous-membrane area distributions 31 to 34 same as those of FIG. 9 are illustrated. Comparing a case where the hue H is compared with data belonging to the reddish mucous membrane based on the yellowish mucous-membrane area distribution with a case where the hue H is compared with data belonging to the reddish mucous membrane based on the reddish mucous-membrane area distribution, relative deviation in the hue direction is increased when the hue H is compared based on the yellowish mucous-membrane area distribution. Therefore, when deviation of data is determined based on the mucous-membrane area distribution and data whose deviation exceeds a threshold is determined as a lesion, and if the deviation of data having the hue H and the saturation S is determined by using an identical criterion, a determination result greatly varies depending on whether the yellowish mucous-membrane area distribution or the reddish mucous-membrane area distribution is used. Therefore, the determination threshold $T_H$ in the hue direction is calculated so that its value is decreased as the hue $H_{Nen}$ of the mucous-membrane-area distribution center is increased, i.e., as the mucous-membrane area distribution comes closer to reddish color. For example, as illustrated in FIG. 11, a determination threshold $T_H$ for the mucous-membrane area distribution 32 is calculated so that it becomes smaller than a determination threshold $T_H$ for the mucous-membrane area distribution 31 whose hue $H_{Nen}$ is smaller than that of the mucous-membrane area distribution 32. Furthermore, a determination threshold $T_H$ for the mucous-membrane area distribution 33 is calculated so that it becomes smaller than the determination threshold $T_H$ for the mucous-membrane area distribution 32 whose hue $H_{Nen}$ is smaller than that of the mucous-membrane area distribution 33.

Moreover, it is assumed that there are pieces of data whose saturation S deviates in the hue direction with respect to the reddish mucous-membrane area distribution. In this case, as the value of the saturation S is increased, data is more likely to correspond to a red lesion even with relatively slight deviation in the hue direction, and such data should be detected as the lesion area. Therefore, the determination threshold $T_H$ in the hue direction is calculated so that its value is decreased as the saturation $S_{Nen}$ of the mucous-membrane-area distribution center is increased. For example, as illustrated in FIG. 11, the determination threshold $T_H$ for the mucous-membrane area distribution 34 is calculated so that it becomes smaller than the determination threshold $T_H$ for the mucous-membrane area distribution 31 whose saturation $S_{Nen}$ is smaller than that of the mucous-membrane area distribution 34.

Figure 12:
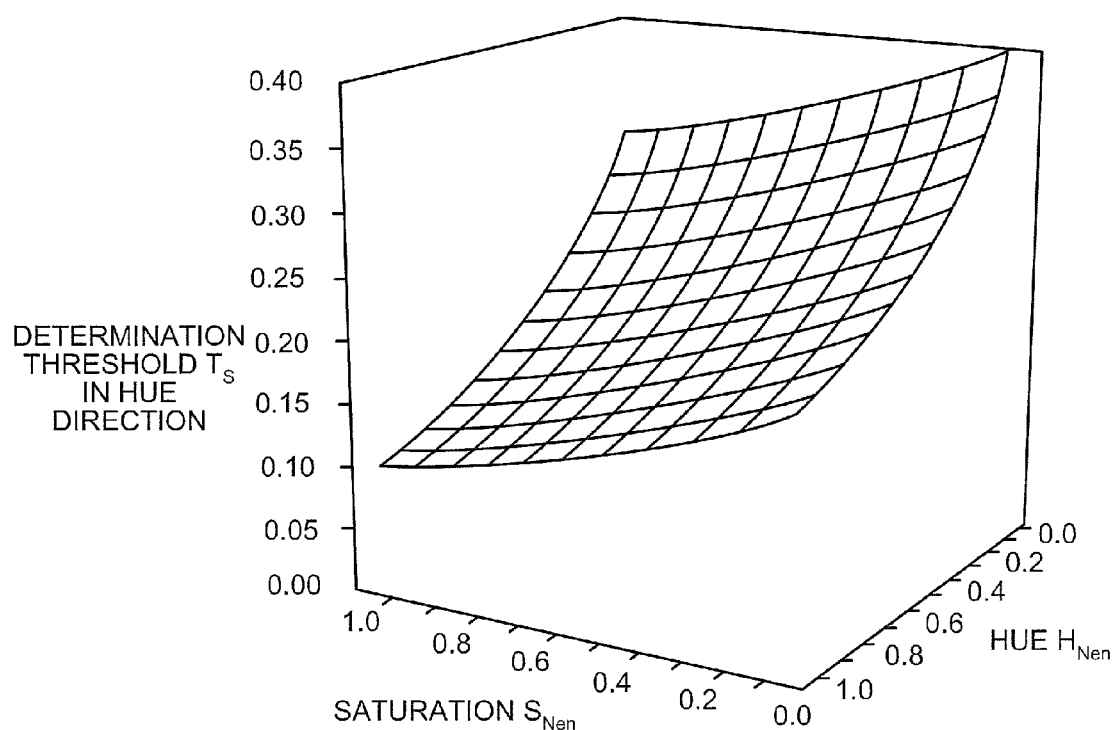
FIG. 12 is a graph of exemplary data of the calculated determination thresholds in the hue direction.

A calculation formula of the determination threshold $T_H$ in the hue direction is represented by the following Equation (7). As represented by the following Equation (7), the calculation formula of the determination threshold $T_H$ in the hue direction is represented by a decreasing function with, for example, the hue $H_{Nen}$, and the saturation $S_{Nen}$ of the mucous-membrane-area distribution center and predetermined coefficients $T_{h2}$ and $T_{s2}$ set in advance. Therefore, the determination threshold $T_N$ in the hue direction is calculated so that it is decreased as the hue $H_{Nen}$ of the mucous-membrane-area distribution center is increased and it is decreased as the saturation $S_{Nen}$ of the mucous-membrane-area distribution center is increased. FIG. 12 is a graph of exemplary data of the saturation $S_{Nen}$ of the mucous-membrane-area distribution center versus the determination threshold $T_H$ in the hue direction actually calculated according to the following Equation (7) based on the saturation $S_{Nen}$ of the mucous-membrane-area distribution center.

$$T_H = (1/(H_{Nen}+1)) \times T_{h2} - S_{Nen} \times T_{s2} \qquad (7)$$

Then, the criterion creating unit 18 creates a criterion $H_{Thresh}$ in the hue direction and a criterion $S_{Thresh}$ in the saturation direction, and sets them as criteria for detecting the lesion area in the processing target image (Step d7). Then, the process returns to Step a7 of FIG. 3 and proceeds to Step a9.

More specifically, the criterion creating unit 18 creates the criterion $H_{Thresh}$ in the hue direction according to the following Equation (8) and the criterion $S_{Thresh}$ in the saturation direction according to the following Equation (9), by using the determination threshold $T_H$ in the hue direction and the determination threshold $T_S$ in the saturation direction.

$$H_{Thresh} = H_{Nen} + T_H \qquad (8)$$

$$S_{Thresh} = S_{Nen} + T_S \qquad (9)$$

For example, as illustrated in FIGS. 9 and 11, regarding the mucous-membrane area distribution 31, a criterion $S_{Thresh}$ with a value 311 and a criterion $H_{Thresh}$ with a value 313 are created. Regarding the mucous-membrane area distribution 32, a criterion $S_{Thresh}$ with a value 321 and a criterion $H_{Thresh}$ with a value 323 are created. Regarding the mucous-membrane area distribution 33, a criterion $S_{Thresh}$ with a value 331 and a criterion $H_{Thresh}$ with a value 333 are created. Regarding the mucous-membrane area distribution 34, a criterion $S_{Thresh}$ with a value 341 and a criterion $H_{Thresh}$ with a value 343 are created.

Figure 13:
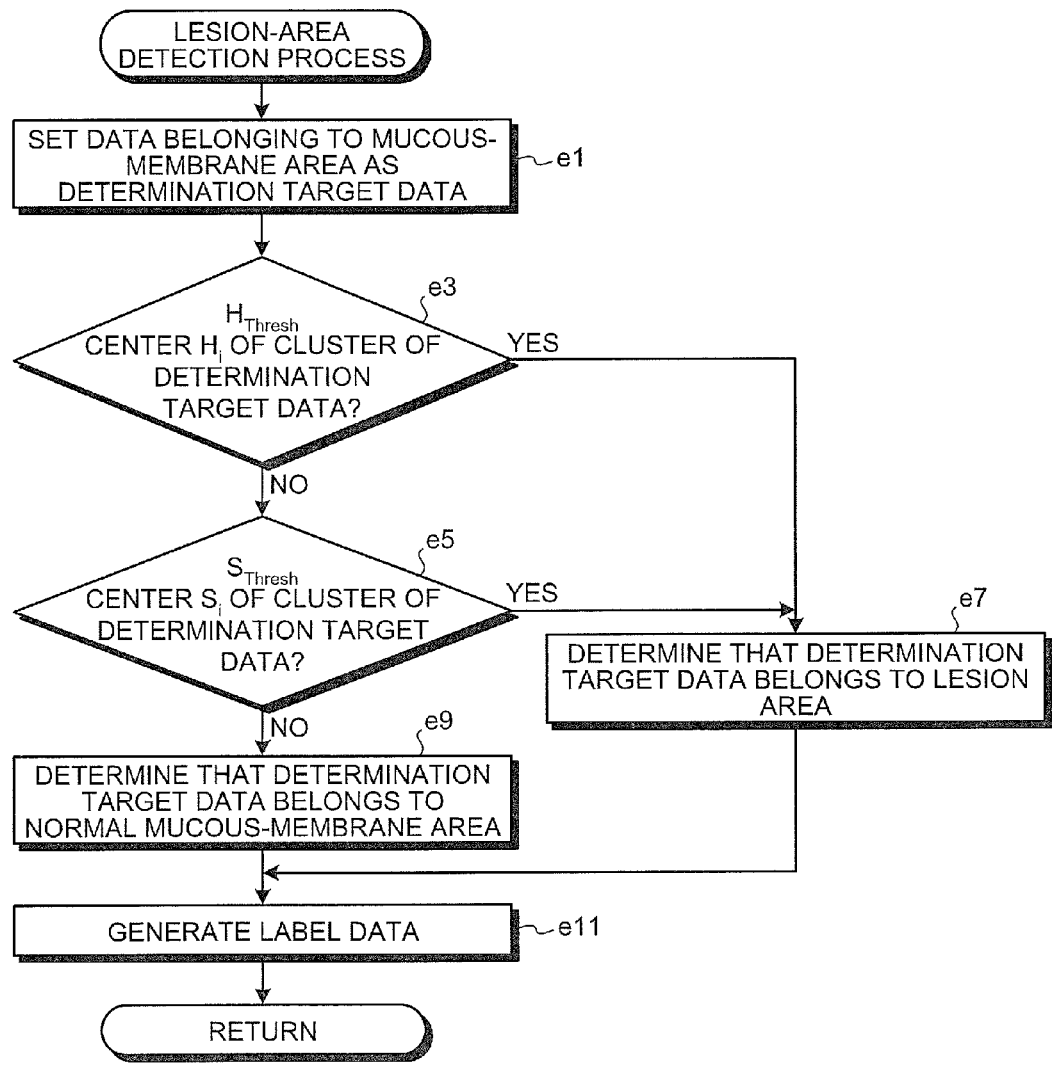
FIG. 13 is a flowchart of a detailed process procedure of a lesion-area detection process.

Next, the lesion-area detection process performed by the lesion-area detecting unit 19 at Step a9 of FIG. 3 is described below. The lesion-area detecting unit 19 determines the data that has been identified as belonging to the mucous-membrane area through the mucous-membrane-area extraction process at Step a5 of FIG. 3, based on the criteria generated through the criterion creation process at Step a7, and detects the lesion area from the processing target image. In practice, the lesion-area detecting unit 19 determines whether the data is the lesion area or not, by using the center $(H_i, S_i)$ of the cluster of data calculated at Step c5 of FIG. 6 and determined as belonging to the mucous-membrane area at Step c7, and the determination criteria $H_{Thresh}$ and $S_{Thresh}$. FIG. 13 is a flowchart of a detailed process procedure of the lesion-area detection process.

As illustrated in FIG. 13, in the lesion-area detection process, the lesion-area detecting unit 19 sets the data belonging to the mucous-membrane area as determination target data (Step e1). Then, the lesion-area detecting unit 19 compares $H_i$ with $H_{Thresh}$, and when $H_{Thresh} \leq H_i$ (YES at Step e3), the process proceeds to Step e7. On the other hand, when $H_{Thresh} \leq H_i$ is not satisfied (NO at Step e3) the lesion-area detecting unit 19 compares $S_i$ with $S_{Thresh}$. When $S_{Thresh} \leq S_i$ (YES at Step e5) the process proceeds to Step e7. At Step e7, the lesion-area detecting unit 19 determines that the determination target data is data belonging to the lesion area. Namely, the lesion-area detecting unit 19 determines that data satisfying $H_{Thresh} \leq H_i$ or $S_{Thresh} \leq S_i$ is the data belonging to the lesion area from among pieces of data belonging to the mucous-membrane area.

Furthermore, when $H_{Thresh} \leq H_i$ is not satisfied (NO at Step e3) and $S_{Thresh} \leq S_i$ is also not satisfied (NO at Step e5), the lesion-area detecting unit 19 determines that the determination target data is data belonging to the normal mucous-membrane area (Step e9). Namely, the lesion-area detecting unit 19 determines that data satisfying $H_{Thresh} > H_i$ and $S_{Thresh} > S_i$ is data belonging to the normal mucous-membrane area from among the pieces of data belonging to the mucous-membrane area.

Figure 14:
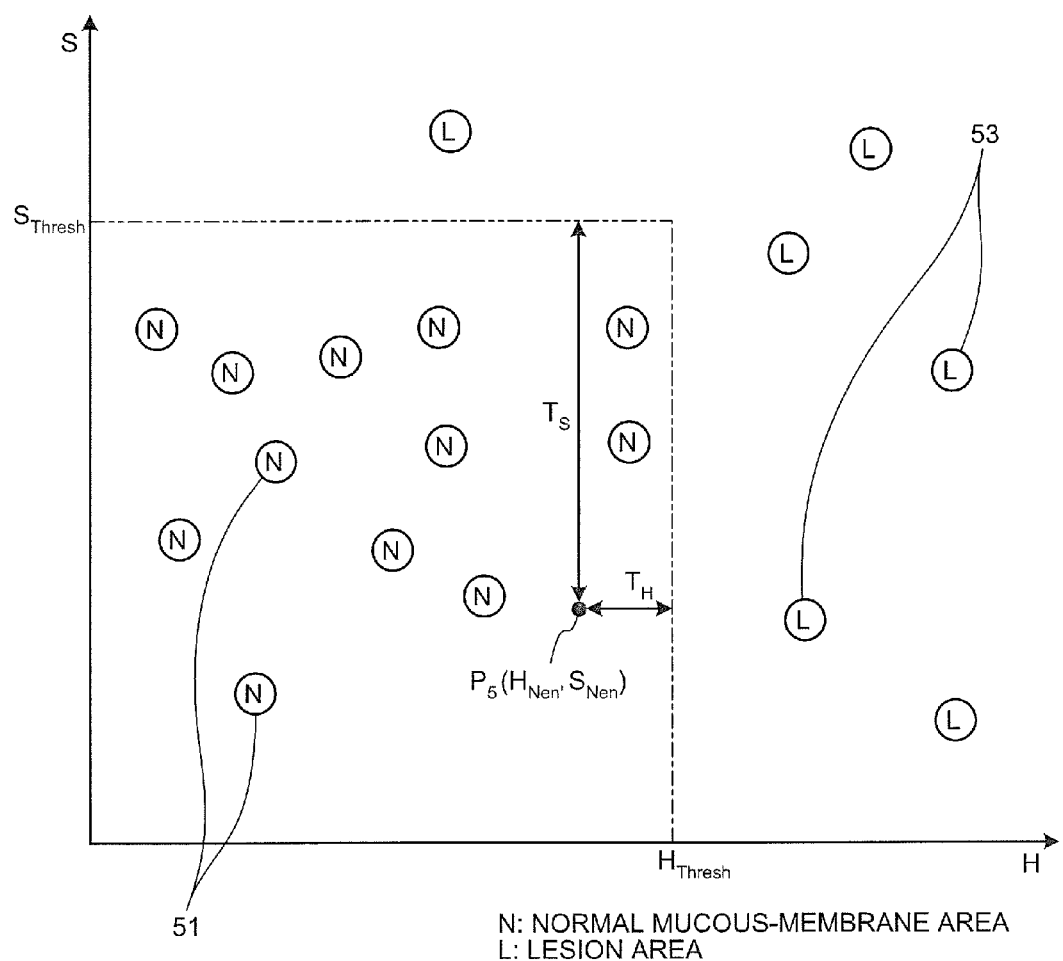
FIG. 14 is a schematic diagram illustrating an example of a detection result of a lesion area.

FIG. 14 is a schematic diagram illustrating an example of the detection result of the lesion area with respect to a single in-vivo image. In FIG. 14, the hue $H_{Nen}$ and the saturation $S_{Nen}$ of a mucous-membrane area distribution center $P_5$ calculated with respect to an in-vivo image as the processing target, and a determination threshold $T_S$ in the saturation direction and a determination threshold $T_H$ in the hue direction calculated based on the mucous-membrane-area distribution center $P_5$ are illustrated. Furthermore, the criterion $H_{Thresh}$ calculated based on the determination threshold $T_H$ in the hue direction is indicated by a chain line, and the criterion $S_{Thresh}$ calculated based on the determination threshold $T_S$ in the saturation direction is indicated by a chain double-dashed line. In the example illustrated in FIG. 14, pieces of data 51 in an area surrounded by the chain line indicating the criterion $H_{Thresh}$ and the chain double-dashed line indicating the criterion $S_{Thresh}$ are determined as data belonging to the normal mucous-membrane area. On the other hand, pieces of data 53 in an area other than the area surrounded by the chain line indicating the criterion $H_{Thresh}$ and the chain double-dashed line indicating the criterion $S_{Thresh}$ are determined as data belonging to the lesion area.

Subsequently, as illustrated in FIG. 13, the lesion-area detecting unit 19 generates label data indicating the lesion area (Step e11). In other words, the lesion-area detecting unit 19 generates the label data by assigning a label indicating the normal mucous-membrane area to a pixel corresponding to data determined as belonging to the normal mucous-membrane area in the in-vivo image, and assigning a label indicating the lesion area to a pixel corresponding to data determined as belonging to the lesion area in the in-vivo image. Then, the process returns to Step a9 of FIG. 3, and proceeds to Step a11.

As described above, according to the first embodiment, it is possible to create the criterion for detecting the lesion area from a processing-target in-vivo image based on respective values of the hue and the saturation of the mucous-membrane area that appears in the in-vivo image as the processing target. More specifically, it is possible to create the criterion in the saturation direction by calculating the determination threshold in the saturation direction so that the determination threshold is decreased as the value of the hue of the mucous-membrane-area distribution center extracted from the in-vivo image as the processing target is increased and the determination threshold is decreased as the value of the saturation of the mucous-membrane-area distribution center is increased. Furthermore, it is possible to create the criterion in the hue direction by calculating the determination threshold in the hue direction so that the determination threshold is decreased as the value of the hue of the mucous-membrane-area distribution center is increased and the determination threshold is decreased as the value of the saturation of the mucous-membrane-area distribution center is increased. Accordingly, the lesion area can be detected from the processing-target in-vivo image by using the generated determination threshold in the hue direction and the generated determination threshold in the saturation direction. Thus, it is possible to adoptively create the criterion depending on respective values of the hue and the saturation of the mucous-membrane area that appears in the in-vivo image. As a result, it is possible to improve the detection precision of the lesion area from the in-vivo image.

The calculation formula of the determination threshold $T_S$ in the saturation direction is not limited by the above-mentioned Equation (6) as long as the determination threshold $T_S$ in the saturation direction is calculated based on at least the hue of the mucous-membrane area. For example, as represented by the following Equation (10), the determination threshold $T_S$ in the saturation direction may be calculated so that its value is decreased as the hue $H_{Nen}$ is increased according to a decreasing function with the hue $H_{Nen}$ of the mucous-membrane-area distribution center and a predetermined coefficient $T_{h1}$ set in advance.

$$T_S = (1/(H_{Nen}+1)) \times T_{h1} \qquad (10)$$

Furthermore, the calculation formula of the determination threshold $T_H$ in the hue direction is not limited by the above-mentioned Equation (7) as long as the determination threshold $T_H$ in the hue direction is calculated based on at least the hue of the mucous-membrane area. For example, the determination threshold $T_H$ in the hue direction may be calculated so that its value is decreased as the hue $H_{Nen}$ is increased according to a decreasing function with the hue $H_{Nen}$ of the mucous-membrane-area distribution center and a predetermined coefficient $T_{h2}$ set in advance.

$$T_H = (1/(H_{Nen}+1)) \times T_{h2} \qquad (11)$$

Figure 15:
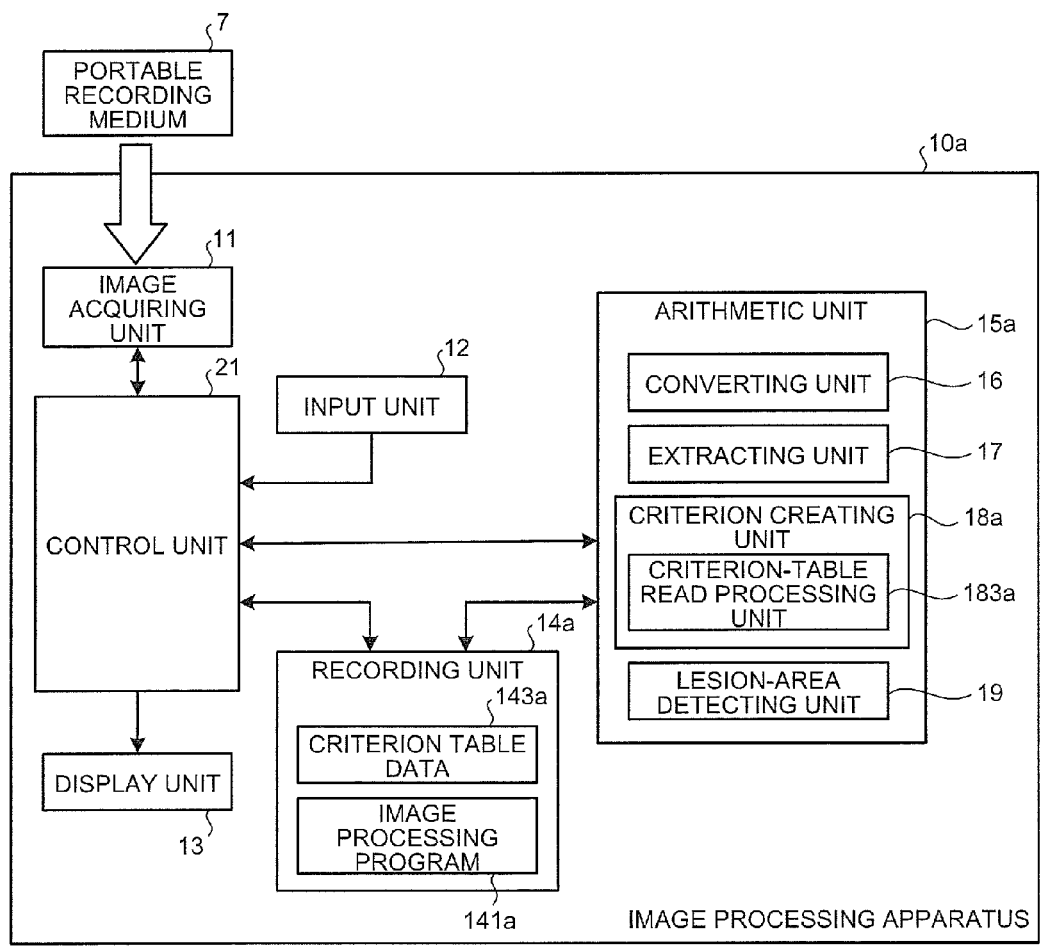
FIG. 15 is a block diagram illustrating a functional configuration of an image processing apparatus according to a second embodiment.

A second embodiment of the present invention will be described below. FIG. 15 is a block diagram illustrating a functional configuration of an image processing apparatus 10a according to the second embodiment. The components identical to those described in the first embodiment are denoted by the same symbols. As illustrated in FIG. 15, the image processing apparatus 10a includes the image acquiring unit 11, the input unit 12, the display unit 13, a recording unit 14a, an arithmetic unit 15a, and the control unit 21 that controls the overall operations of the image processing apparatus 10a.

The recording unit 14a records therein, as a criterion-table recording unit, a criterion table data 143a. The recording unit 14a also records therein an image processing program 141a for detecting a lesion area in an in-vivo image by using a criterion read out from the criterion table data 143a.

The criterion table data 143a contains a criterion table of the determination thresholds $T_S$, in which a value of the determination threshold $T_S$ in the saturation direction is set in association with respective values of the saturation $S_{Nen}$ and the hue $H_{Nen}$, and a criterion table of the determination thresholds $T_H$, in which a value of the determination threshold $T_H$ in the hue direction is set in association with respective values of the saturation $S_{Nen}$ and the hue $H_{Nen}$.

Figures 16, 17:
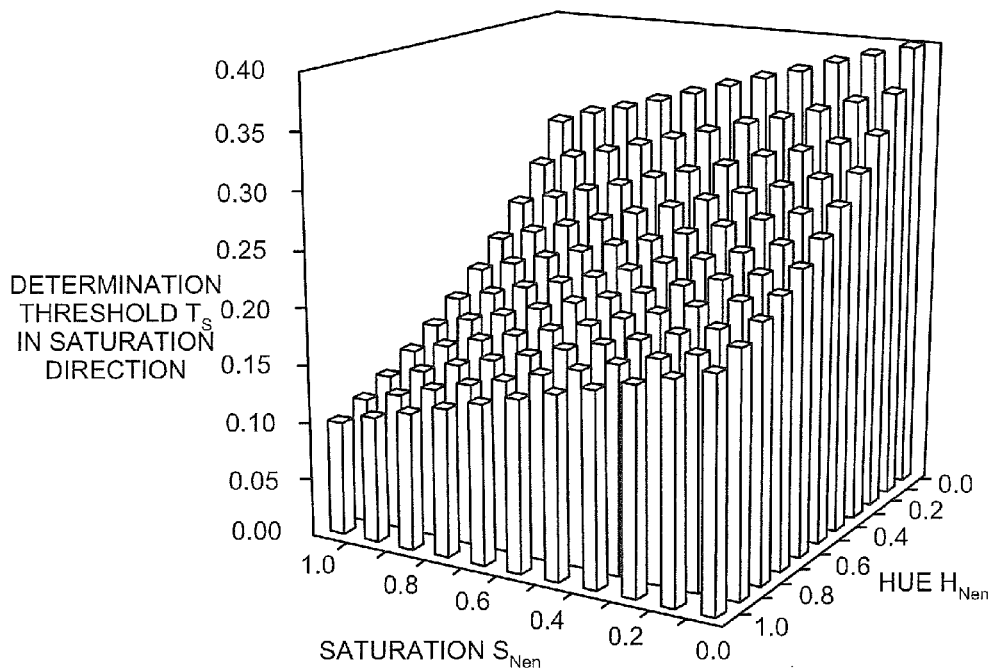
FIG. 16 illustrates an exemplary data structure of a criterion table of determination thresholds in the saturation direction.
FIG. 17 is a graph of data in the criterion table of the determination thresholds in the saturation direction illustrated in FIG. 16.

FIG. 16 illustrates an exemplary data structure of the criterion table of the determination thresholds TS in the saturation direction. FIG. 17 is a graph of data in the criterion table of the determination thresholds $T_S$ in the saturation direction illustrated in FIG. 16. In the criterion table of the determination thresholds $T_S$ in the saturation direction, a plurality of determination thresholds $T_S$ in the saturation direction, which are calculated in advance so that they are decreased as the hue $H_{Nen}$ of the mucous-membrane-area distribution center is increased and they are decreased as the saturation $S_{Nen}$ of the mucous-membrane-area distribution center is increased in the similar manner as that of the first embodiment, are set in association with respective pairs of the hue $H_{Nen}$ and the saturation $S_{Nen}$ used for calculating respective thresholds.

Figures 18, 19:
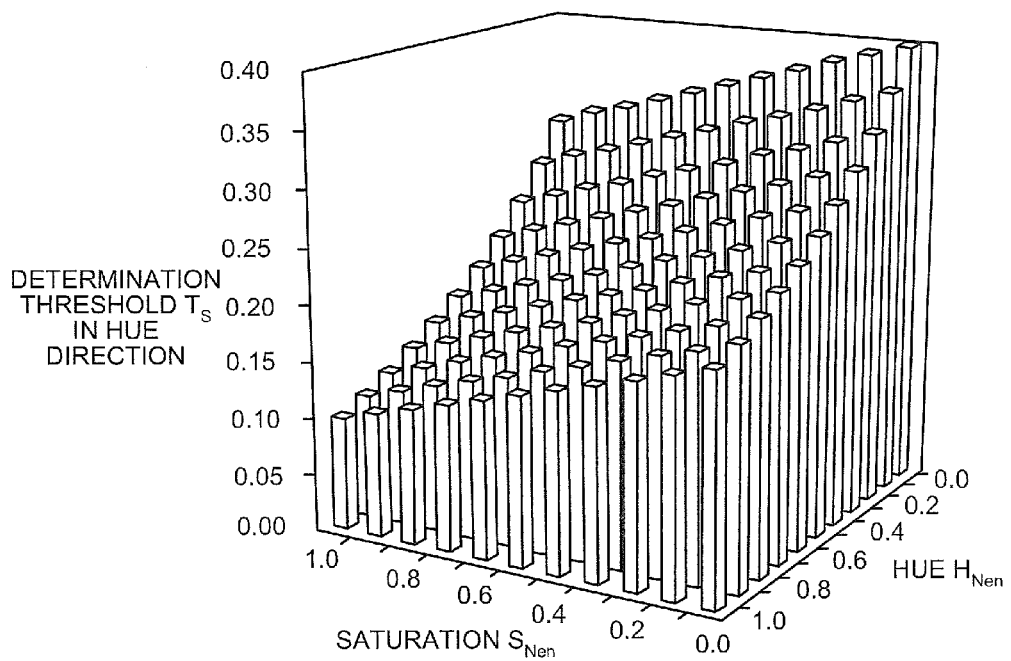
FIG. 18 illustrates an exemplary data structure of a criterion table of determination thresholds in the hue direction.
FIG. 19 is a graph of data in the criterion table of the determination thresholds in the hue direction illustrated in FIG. 18.

FIG. 18 illustrates an exemplary data structure of the criterion table of the determination thresholds TH in the hue direction. FIG. 19 is a graph of data in the criterion table of the determination thresholds $T_H$ in the hue direction illustrated in FIG. 18. In the criterion table of the determination thresholds $T_H$ in the hue direction, a plurality of determination thresholds $T_H$ in the hue direction, which are calculated in advance so that they are decreased as the hue $H_{Nen}$ of the mucous-membrane-area distribution center is increased and they are decreased as the saturation $S_{Nen}$ of the mucous-membrane-area distribution center is increased in the similar manner as that of the first embodiment, are set in association with respective pairs of the hue $H_{Nen}$ and the saturation $S_{Nen}$ used for calculating respective thresholds.

Furthermore, the arithmetic unit 15a includes the converting unit 16, the extracting unit 17 as the body-tissue extracting unit, a criterion creating unit 18a, and the lesion-area detecting unit 19 as the detecting unit. In the second embodiment, the criterion creating unit 18a includes a criterion-table read processing unit 183a as a criterion table reading unit. The criterion-table read processing unit 183a reads out a corresponding determination threshold $T_S$ in the saturation direction and a corresponding determination threshold $T_H$ in the hue direction from the criterion table data 143a based on the hue H and the saturation S of the mucous-membrane area.

Figure 20:
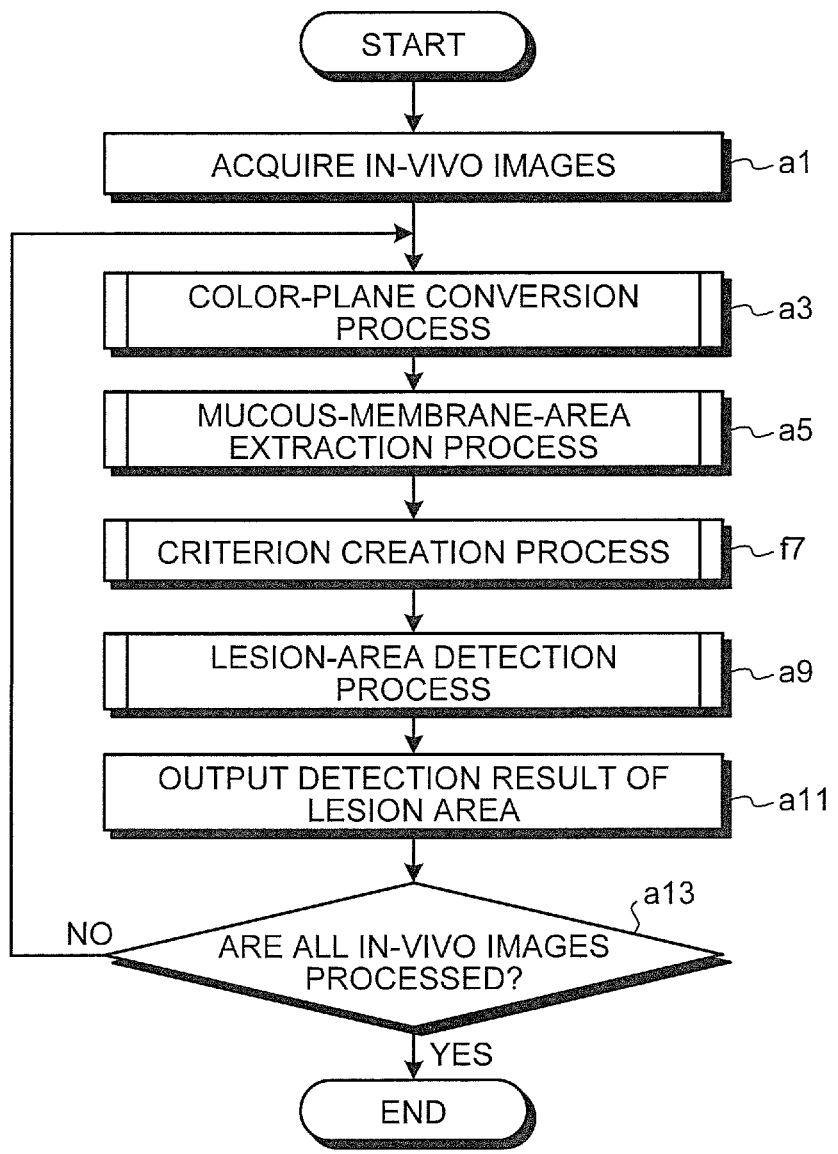
FIG. 20 is an overall flowchart of a process procedure performed by the image processing apparatus according to the second embodiment.

FIG. 20 is an overall flowchart of a process procedure performed by the image processing apparatus 10a according to the second embodiment. The processes described below are realized by causing the arithmetic unit 15a to execute the image processing program 141a recorded in the recording unit 14a. In FIG. 20, the process procedures identical to those of the first embodiment are denoted by the same symbols.

Figure 21:
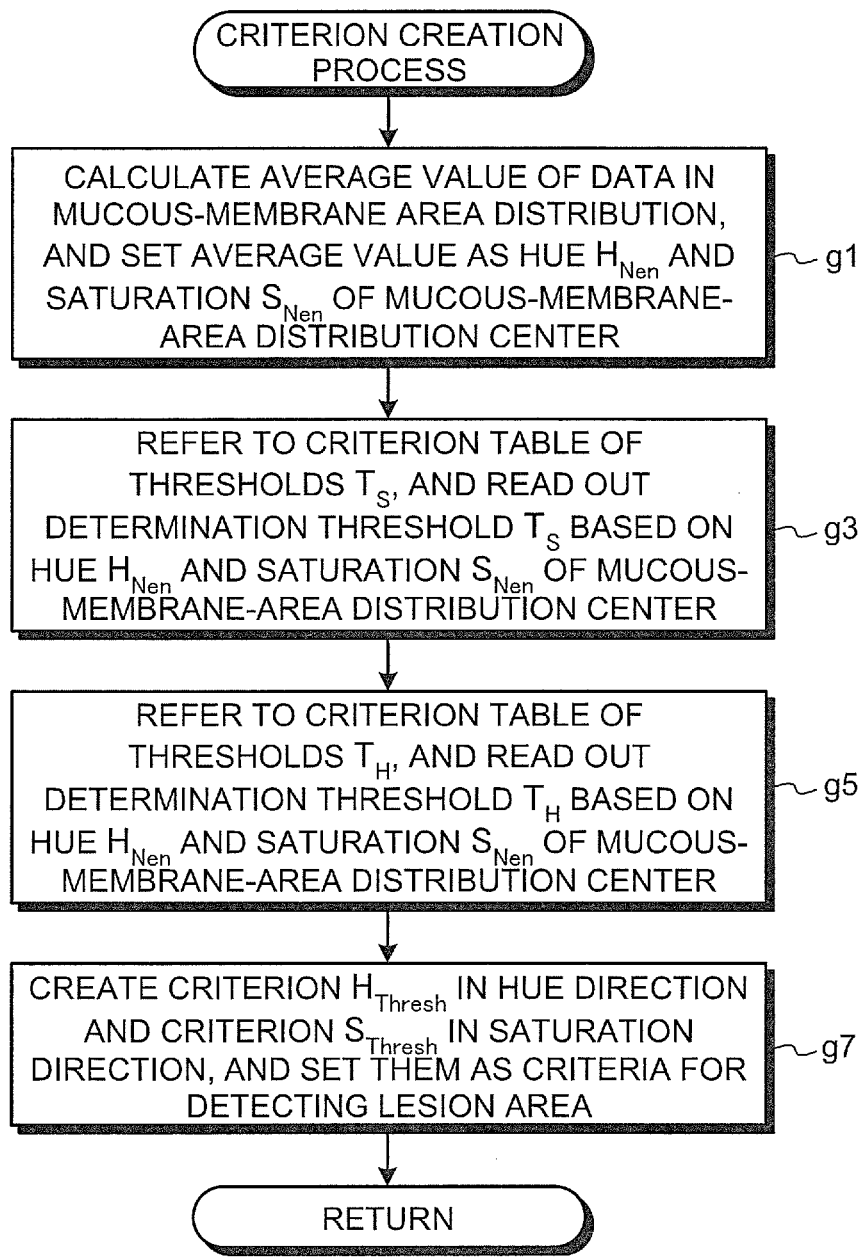
FIG. 21 is a flowchart of a detailed process procedure of a criterion creation process according to the second embodiment.

In the second embodiment, after the mucous-membrane-area extraction process at Step a5, the criterion creating unit 18a performs a criterion creation process (Step f7). Subsequently, the process proceeds to Step a9. FIG. 21 is a flowchart of a detailed process procedure of the criterion creation process according to the second embodiment.

As illustrated in FIG. 21, in the criterion creation process of the second embodiment, the criterion creating unit 18a calculates an average value of data determined as belonging to the mucous-membrane area distribution and sets the calculated average value as the hue $H_{Nen}$ and the saturation $S_{Nen}$ of the center of the mucous-membrane area (mucous-membrane-area distribution center) similarly to the first embodiment (Step g1).

Subsequently, the criterion-table read processing unit 183a of the criterion creating unit 18a refers to the criterion table of the determination thresholds $T_S$ in the saturation direction in the criterion table data 143a, and reads out a corresponding determination threshold $T_S$ in the saturation direction based on the hue $H_{Nen}$ and the saturation $S_{Nen}$ of the mucous-membrane-area distribution center (Step g3).

Then, the criterion-table read processing unit 183a refers to the criterion table of the determination thresholds $T_H$ in the hue direction in the criterion table data 143a, and reads out a corresponding determination threshold $T_H$ in the hue direction based on the hue $H_{Nen}$ and the saturation $S_{Nen}$ of the mucous-membrane-area distribution center (Step g5).

The criterion creating unit 18a then creates a criterion for detecting a lesion area in the processing target image by calculating the criterion $H_{Thresh}$ in the hue direction and the criterion $S_{Thresh}$ in the saturation direction in the same manner as that of the first embodiment (Step g7). At this time, the criterion creating unit 18a uses the read determination threshold $T_H$ in the hue direction and the read determination threshold $T_S$ in the saturation direction.

As described above, according to the second embodiment, it is possible to set the determination threshold $T_H$ in the hue direction and the determination threshold $T_S$ in the saturation direction in association with a pair of the hue $H_{Nen}$ and the saturation $S_{Nen}$. Therefore, it is possible to achieve the same effects as those of the first embodiment. Furthermore, it is not necessary to calculate respective values of the determination threshold $T_H$ in the hue direction and the determination threshold $T_S$ in the saturation direction per processing. As a result, a processing load can be reduced.

In the above-mentioned second embodiment, it is described that the criterion table data 143a contains the criterion table of the determination thresholds $T_S$, in which the plurality of determination thresholds $T_S$ in the saturation direction are set in association with respective pairs of the hue $H_{Nen}$ and the saturation $S_{Nen}$ used for calculating the respective values, and the criterion table of the determination thresholds $T_H$, in which the plurality of determination thresholds $T_H$ in the hue direction are set in association with respective pairs of hue $H_{Nen}$ and the saturation $S_{Nen}$ used for calculating the respective values. In contrast, it is possible to calculate the determination threshold $T_S$ in the saturation direction according to Equation (10) described above as a modified example of the first embodiment, and prepare the criterion table of the determination threshold $T_S$ such that the determination threshold $T_S$ is set in association with a value of the hue $H_{Nen}$ used for calculating the value of the determination threshold $T_S$. In this case, the criterion-table read processing unit 183*a* reads out a corresponding determination threshold $T_S$ in the saturation direction based on the hue $H_{Nen}$ of the mucous-membrane-area distribution center. It is also possible to calculate a value of the determination threshold $T_H$ in the hue direction according to the above-mentioned Equation (11), and prepare the criterion table of the determination thresholds $T_H$ such that the determination threshold $T_H$ is set in association with a value of the hue $H_{Nen}$ used for calculating the value of the determination threshold $T_H$. In this case, the criterion-table read processing unit 183*a* reads out a corresponding determination threshold $T_H$ in the hue direction based on the hue $H_{Nen}$ of the mucous-membrane-area distribution center.

Figure 22:
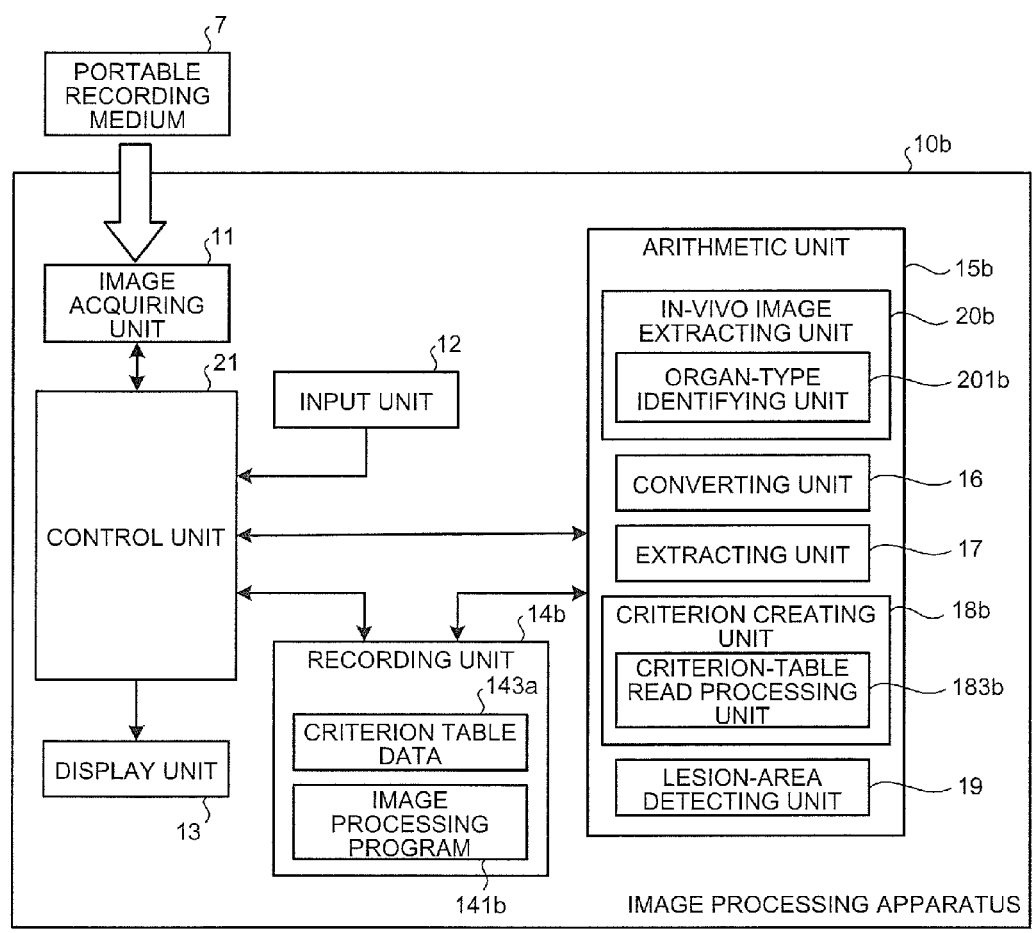
FIG. 22 is a block diagram illustrating a functional configuration of an image processing apparatus according to a third embodiment.

A third embodiment of the present invention will be described below. FIG. 22 is a block diagram illustrating a functional configuration of an image processing apparatus 10*b* according to the third embodiment. The components identical to those described in the first and the second embodiments are denoted by the same symbols. As illustrated in FIG. 22, the image processing apparatus 10*b* includes the image acquiring unit 11, the input unit 12, the display unit 13, a recording unit 14*b*, an arithmetic unit 15*b*, and the control unit 21 that controls the overall operations of the image processing apparatus 10*b*.

The recording unit 14*b* records therein the criterion table data 143*a* described in the second embodiment. The recording unit 14*b* also includes an image processing program 141*b* for detecting a lesion area by identifying a type of an organ that appears in an in-vivo image and extracting the in-vivo image for each organ type.

The arithmetic unit 15*b* includes an in-vivo image extracting unit 20*b*, the converting unit 16, the extracting unit 17 as the body-tissue extracting unit, a criterion creating unit 18*b*, and the lesion-area detecting unit 19 as the detecting unit. The in-vivo image extracting unit 20*b* extracts in-vivo images determined as having identical organ types from a series of in-vivo images. The in-vivo image extracting unit 20*b* includes an organ-type identifying unit 201*b* that identifies a type of an organ (organ type) that appears in each in-vivo image. In the third embodiment, the criterion creating unit 18*b* includes a criterion-table read processing unit 183*b*, and creates a criterion per organ type.

Figure 23:
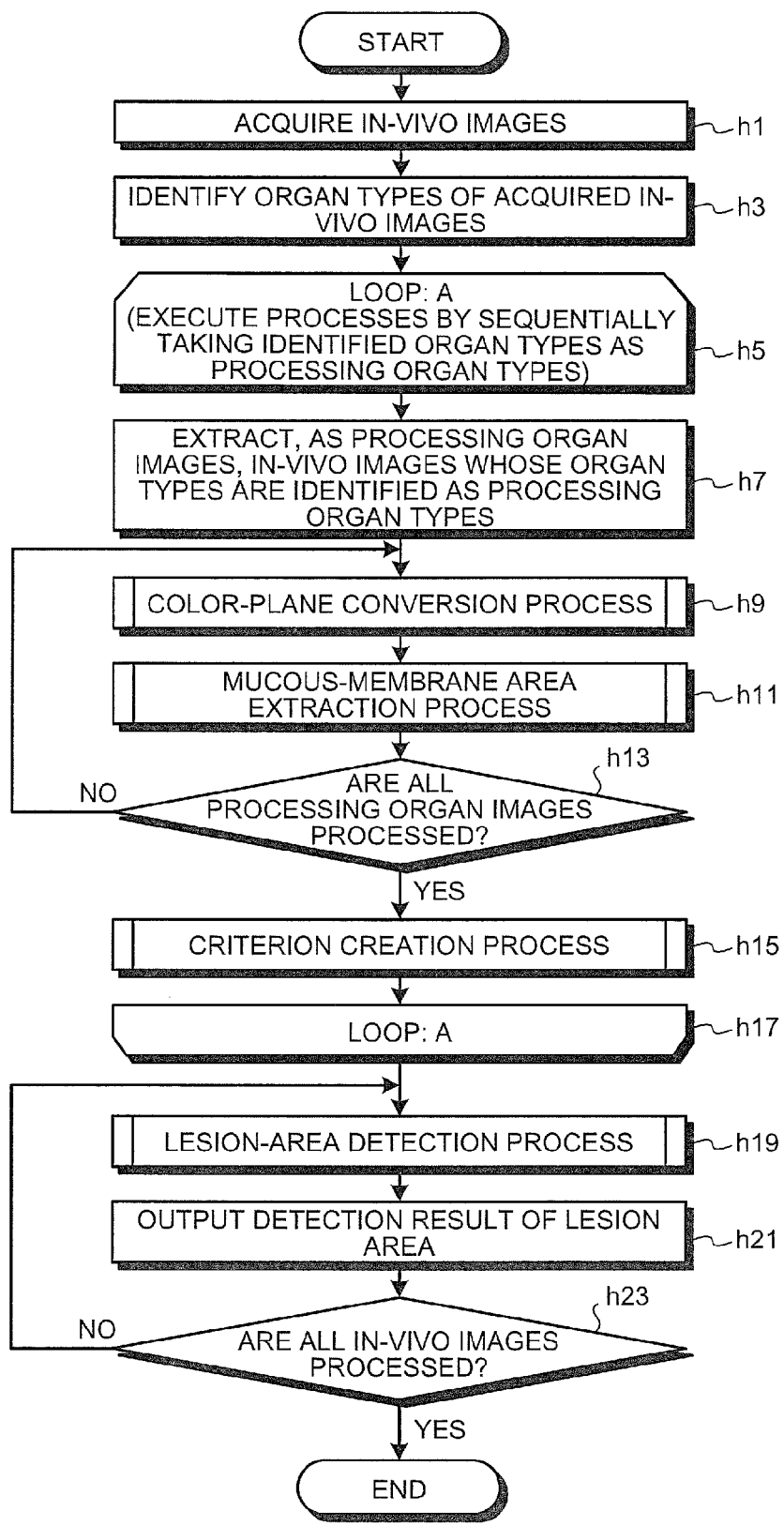
FIG. 23 is an overall flowchart of a process procedure performed by the image processing apparatus according to the third embodiment.

FIG. 23 is an overall flowchart of a process procedure performed by the image processing apparatus 10*b* according to the third embodiment. The processes described below are realized by causing the arithmetic unit 15*b* to execute the image processing program 141*b* recorded in the recording unit 14*b*.

As illustrated in FIG. 23, the arithmetic unit 15*b* acquires a series of in-vivo images by the same procedure as that of the first embodiment (Step h1). Subsequently, the organ-type identifying unit 201*b* identifies organ types that appear in each in-vivo image constituting the acquired series of in-vivo images (Step h3). In this example, four types such as an esophagus, a stomach, a small intestine, and a large intestine are identified as the organ types that appear in each in-vivo image.

As a specific method of identifying the organ types, a known technique may be used appropriately. For example, a technique disclosed in Japanese Laid-open Patent Publication No. 2006-288612 may be used for identifying the organ types based on an average R value, an average G value, and an average B value of the in-vivo image. More specifically, respective value ranges for the average R value, the average G value, and the average B value are set for each organ type in advance. In the third embodiment, because four organ types such as the esophagus, the stomach, the small intestine, and the large intestine are to be identified, the respective value ranges for the average R value, the average G value, and the average B value are set for each of the esophagus, the stomach, the small intestine, and the large intestine. Then, when the average R value, the average G value, and the average B value of the in-vivo image are respectively within the value ranges for the esophagus, the organ type of the observed area that appears in the in-vivo image is identified as the esophagus. When the average R value, the average G value, and the average B value of the in-vivo image are respectively within the value ranges for the stomach, the organ type of the observed area that appears in the in-vivo image is identified as the stomach. When the average R value, the average G value, and the average B value of the in-vivo image are respectively within the value ranges for the small intestine, the organ type of the observed area that appears in the in-vivo image is identified as the small intestine. When the average R value, the average G value, and the average B value of the in-vivo image are respectively within the value ranges for the large intestine, the organ type of the observed area that appears in the in-vivo image is identified as the large intestine. As long as the organ types that appear in an image can be identified, the method is not limited by the above-mentioned method, and any other methods are applicable.

Subsequently, a loop-A process is performed by sequentially taking the identified four organ types such as the esophagus, the stomach, the small intestine, and the large intestine as a processing organ type (Steps h5 to h17).

More specifically, the in-vivo image extracting unit 20*b* extracts, as processing organ images, in-vivo images whose organ types are identified as the processing organ types from the series of in-vivo images (Step h7). Then, the processing organ images extracted at Step h7 are sequentially read out one by one from the recording unit 14*b*. The converting unit 16 performs the color-plane conversion process on the read processing organ images by the same procedure as that of the first embodiment (Step h9). Subsequently, the extracting unit 17 performs the mucous-membrane-area extraction process by the same procedure as that of the first embodiment (Step h11). Then, it is determined whether all the processing organ images extracted at Step h7 are processed. When an unprocessed processing organ image is present (NO at Step h13), the process returns to Step h9, and the process from Step h9 to Step h11 is performed on the unprocessed processing organ image. On the other hand, when all the extracted processing organ images are processed (YES at Step h13), the criterion creating unit 18*b* performs a criterion creation process (Step h15).

After the loop-A process is performed by taking each organ type as the processing organ type, and a criterion for each organ type is created, the series of in-vivo images acquired at Step h1 and recorded in the recording unit 14*b* are sequentially read out one by one. Then, the lesion-area detecting unit 19 performs the lesion-area detection process by taking the read in-vivo image as the processing target (Step h19). In the lesion-area detection process, values calculated for the organ type of the processing target image through the criterion creation process at Step h15 are used as the criterion in the hue direction and the criterion in the saturation direction. The process procedure is the same as that of the first embodiment.

Subsequently, the arithmetic unit 15b outputs a detection result of the lesion area with respect to the in-vivo image as the processing target (Step h21). Then, the arithmetic unit 15b determines whether the process from Step h19 to Step h21 is performed by taking all the in-vivo images acquired at Step h1 as the processing targets. When an unprocessed in-vivo image is present (NO at Step h23), the process returns to Step h19 by taking the unprocessed in-vivo image as the processing target image, and the above-mentioned process is repeated. On the other hand, when all the in-vivo images are processed (YES at Step h23), the process by the arithmetic unit 15b of the image processing apparatus 10b is terminated.

Figure 24:
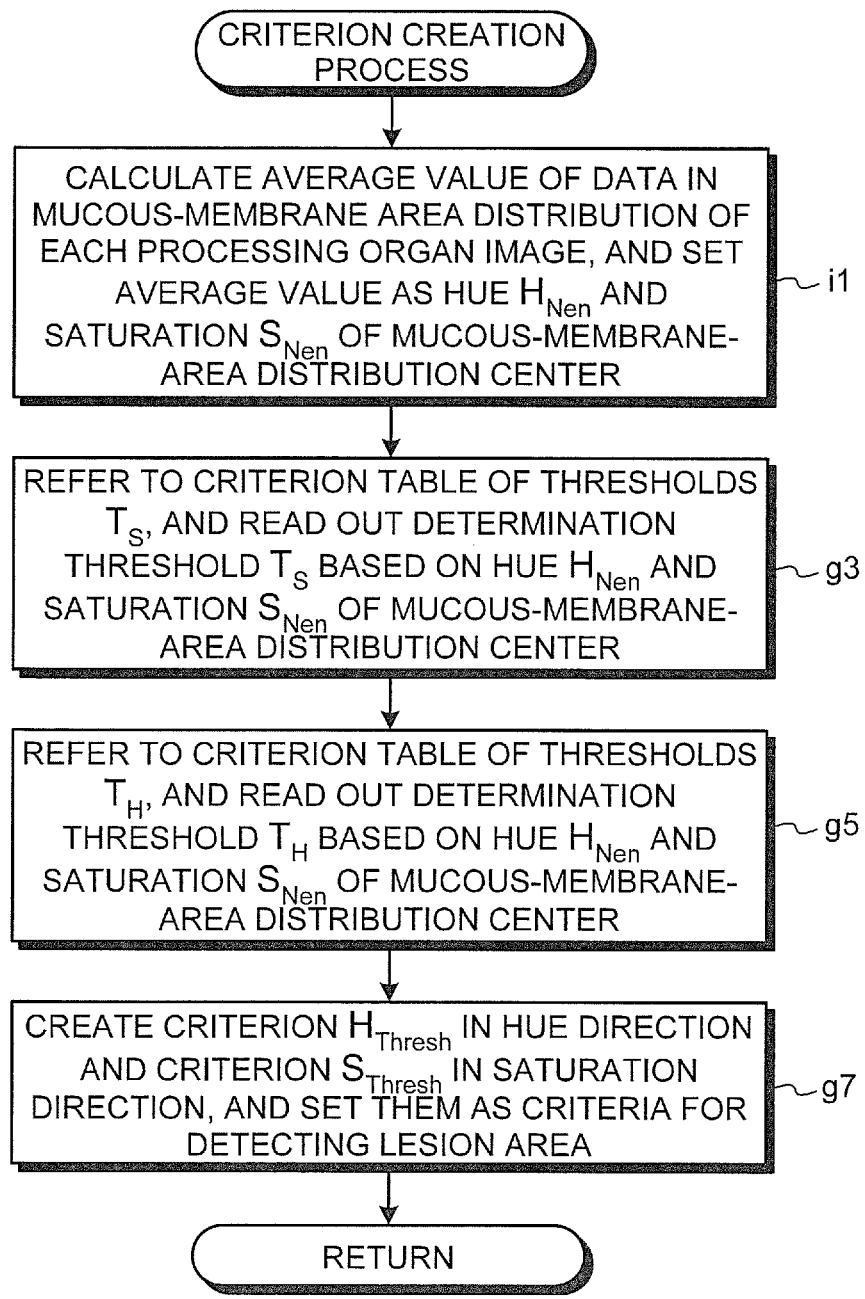
FIG. 24 is a flowchart of a detailed process procedure of a criterion creation process according to the third embodiment.

Next, the criterion creation process at Step h15 of FIG. 23 is described below. FIG. 24 is a flowchart of a detailed process procedure of the criterion creation process according to the third embodiment. In FIG. 24, the process procedures identical to those of the second embodiment are denoted by the same symbols.

As illustrated in FIG. 24, in the criterion creation process according to the third embodiment, the criterion creating unit 18b calculates an average value of data belonging to the mucous-membrane area distribution of each processing organ image, and sets the calculated average value to the hue $H_{Nen}$ and the saturation $S_{Nen}$ of the center of the mucous-membrane area distribution (mucous-membrane-area distribution center) (Step i1). For example, it is possible to calculate an average value of all pieces of data belonging to the mucous-membrane area distribution of each processing organ image, or it is possible to select some pieces of data from each mucous-membrane area distribution of each processing organ image and calculate an average value of the selected pieces of data. Then, the process proceeds to Step g3.

In the above-mentioned first and the second embodiments, it is described that the mucous-membrane area distribution is obtained by extracting the mucous-membrane area per in-vivo image, and then the criterion is created based on the mucous-membrane area distribution. However, when the mucous-membrane area distribution is obtained by extracting the mucous-membrane area per in-vivo image in this manner, and if bleeding appears in the whole in-vivo image for example, the mucous-membrane area distribution is obtained with a large number of pieces of data corresponding to a bleeding portion contained. Therefore, in some cases, these pieces of data corresponding to the bleeding portion may not be obtained as data deviating from the mucous-membrane area distribution, and may not be detected as the lesion area. In contrast, according to the third embodiment, because the criterion is created by using the mucous-membrane area distribution of the mucous-membrane area extracted from all the in-vivo images identified as having identical organ types, the criterion can be created per organ type. Consequently, the criterion for each organ type can be applied to in-vivo images containing corresponding organs. Therefore, even when an in-vivo image having the bleeding portion all over its area is contained in the in-vivo images identified as having identical organ types, variation between images can be prevented and the bleeding portion can stably be detected as the lesion area.

Furthermore, because compositions of actual mucosal membrane differ between organs, colors of the mucous-membrane area vary depending on the organ types. According to the third embodiment, because the criterion can be created per organ type having similar color, the lesion area can be detected with good precision. If the criterion is created based on the mucous-membrane area distribution of the mucous-membrane areas in different colors, the mucous-membrane area distribution may be widened in the color plane. As a result, the criterion may not be calculated accurately.

Figure 25:
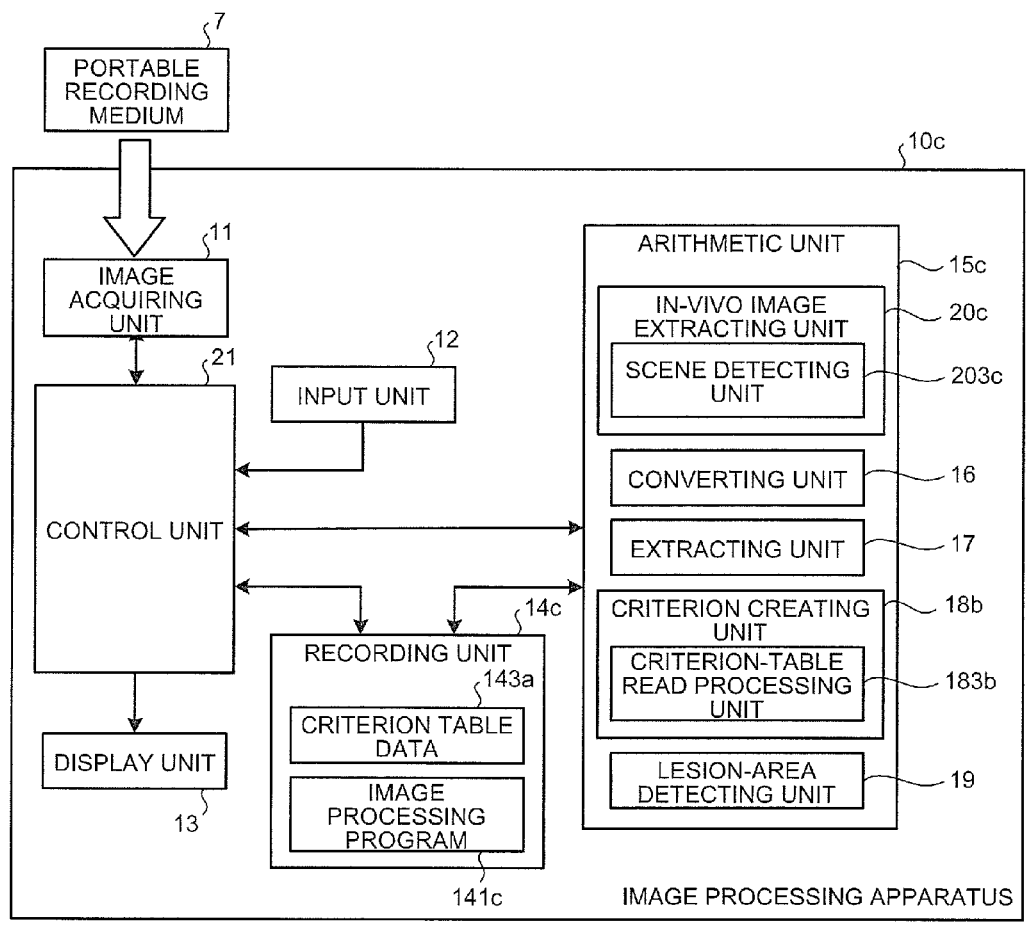
FIG. 25 is a block diagram illustrating a functional configuration of an image processing apparatus according to a fourth embodiment.

A fourth embodiment of the present invention will be described below. FIG. 25 is a block diagram illustrating a functional configuration of an image processing apparatus 10c according to the fourth embodiment. The components identical to those described in the first to the third embodiments are denoted by the same symbols. As illustrated in FIG. 25, the image processing apparatus 10c includes the image acquiring unit 11, the input unit 12, the display unit 13, a recording unit 14c, an arithmetic unit 15c, and the control unit 21 that controls the overall operations of the image processing apparatus 10c.

The recording unit 14c records therein the criterion table data 143a described in the second embodiment. The recording unit 14c also records therein an image processing program 141c for detecting a lesion area by detecting a successive image interval in which change in a scene is small from a series of in-vivo images and extracting an in-vivo image per detected successive image.

The arithmetic unit 15c includes an in-vivo image extracting unit 20c, the converting unit 16, the extracting unit 17 as the body-tissue extracting unit, the criterion creating unit 18b, and the lesion-area detecting unit 19 as the detecting unit. The in-vivo image extracting unit 20c extracts in-vivo images identified as having identical organ types from the series of in-vivo images. The in-vivo image extracting unit 20c includes a scene detecting unit 203c as a scene-change detecting unit that detects the successive image interval in which change in a scene is small from the series of in-vivo images.

FIG. 26 is an overall flowchart of a process procedure performed by the image processing apparatus 10c according to the fourth embodiment. The processes described below are realized by causing the arithmetic unit 15c to execute the image processing program 141c recorded in the recording unit 14c. In FIG. 26, the process procedures identical to those of the third embodiment are denoted by the same symbols.

As illustrated in FIG. 26, the arithmetic unit 15c acquires a series of in-vivo images by the same procedure as that of the first embodiment (Step h1). Subsequently, the scene detecting unit 203c detects, as a successive image interval, an interval in which change in a scene is small from the acquired series of in-vivo images (Step j3).

As a specific method of detecting the change in a scene, a known technique can be used appropriately. For example, as a specific calculation method, a difference in luminance values between adjacent images is obtained, and when the difference in the luminance values is equal to or larger than a threshold set in advance, it is determined that the scene has changed greatly. When the difference in the luminance values is smaller than the threshold set in advance, it is determined that the scene has not changed or the change in the scene is small. The scene detecting unit 203c determines magnitude of the change in the scene by the above-mentioned method for each in-vivo image constituting the series of in-vivo images. Then, the scene detecting unit 203c detects an interval in which the scene has not changed or the change in the scene is small as the successive image interval from the series of in-vivo images. As long as the interval in which the scene has not changed or the change in the scene is small can be detected from the series of in-vivo images, the method is not limited by the above-mentioned method, and any other methods are applicable.

Subsequently, a loop-B process is performed by sequentially taking the detected successive image intervals as processing intervals (Step j5 to Step j17).

More specifically, the in-vivo image extracting unit 20c extracts, as processing interval images, in-vivo images belonging to the processing interval from the series of in-vivo images (Step j7). Then, the processing interval images extracted at Step j7 are sequentially read out one by one from the recording unit 14c, and the process proceeds to Step h9.

When the process from Step h9 to Step h11 is performed on all the processing interval images extracted at Step j7 (YES at Step j13), the criterion creating unit 18b performs a criterion creation process. The criterion creation process can basically be realized by the same process procedure as that of the third embodiment. However, in the process at Step i1 of FIG. 24, an average value of all pieces of data of the mucous-membrane area distribution of each processing interval image is calculated, and the calculated average value is set as the hue $H_{Nen}$ and the saturation $S_{Nen}$ of the center of the mucous-membrane area distribution (mucous-membrane-area distribution center).

After the loop-B process is performed by taking each successive image interval as the processing interval and the criterion is created for each successive image interval, the series of in-vivo images acquired at Step h1 and recorded in the recording unit 14c are sequentially read out one by one. Then, the lesion-area detecting unit 19 performs the lesion-area detection process by taking the read in-vivo image as the processing target (Step j19). In the lesion-area detection process, values calculated for the successive image interval to which the processing target image belongs through the criterion creation process at Step j15 are used as the criterion in the hue direction and the criterion in the saturation direction. The process procedure is the same as that of the first embodiment.

Subsequently, the arithmetic unit 15c outputs a detection result of the lesion area with respect to the in-vivo image as the processing target (Step j21). Then, the arithmetic unit 15c determines whether the process from Step j19 to Step j21 is performed by taking all the in-vivo images acquired at Step h1 as the processing target. When an unprocessed in-vivo image is present (NO at Step j23), the process returns to Step j19 by taking the unprocessed in-vivo image as the processing target image, and the above-mentioned process is repeated. On the other hand, when all the in-vivo images are processed (YES at Step j23), the process by the arithmetic unit 15c of the image processing apparatus 10c is terminated.

When the scene has changed greatly, it means that the capsule endoscope has moved largely. When the capsule endoscope has moved largely, location of imaged organs has been changed accordingly. Furthermore, as described above, compositions of actual mucous membrane vary depending on organs. Therefore, when organs as imaging targets are changed because of large movement of the capsule endoscope, colors of the mucous-membrane areas that appear in the in-vivo images are changed before and after the change in the scene. According to the fourth embodiment, a criterion can be created per successive image interval in which the change in a scene is small by using the mucous-membrane area distribution of the mucous-membrane area extracted from all the in-vivo images belonging to the successive image interval. Furthermore, the criterion created per successive image interval can be applied to each in-vivo image belonging to a corresponding successive image interval. Therefore, it is possible to create the criterion appropriately per successive image interval. As a result, variation between the images can be prevented and the lesion area can stably be detected.

In the above-mentioned third embodiment, it is described that the criterion is created by extracting all the in-vivo images identified as having identical organ types as the processing organ images and then extracting the mucous-membrane area. On the other hand, it is possible to extract, as the processing organ images, two or more predetermined number of in-vivo images from the in-vivo images identified as having identical organ types. Furthermore, in the fourth embodiment, it is described that the criterion is generated by extracting all the in-vivo images belonging to an identical successive image interval as the processing interval images and then extracting the mucous-membrane area. On the other hand, it is possible to extract, as the processing interval images, two or more predetermined number of in-vivo images from among the in-vivo images belonging to the identical successive image interval.

In each embodiment described above, it is explained that the lesion area is detected from the in-vivo image captured by the capsule endoscope. However, the in-vivo image to be processed is not limited to the image captured by the capsule endoscope. For example, it is possible to process an in-vivo image captured by other medical equipments such as endoscopes.

Moreover, in each embodiment described above, it is explained that the hue and the saturation are used as the feature data, and the criterion in the hue direction and the criterion in the saturation direction are created as the criteria for detecting the lesion area from the in-vivo image. However, the feature data applicable to the present invention is not limited to the hue and the saturation. For example, it is possible to use the R value, the G value, and the B value of each pixel of the in-vivo image as the feature data, and create a criterion for each feature data. It is also possible to use other values corresponding to the hue and the saturation as the feature data. For example, it is possible to obtain color ratio data (G/R) by dividing the G value by the R value or color ratio data (B/G) by dividing the B value by the G value, and create a criterion by taking each color ratio data as the feature data. In this case, it is possible to calculate a determination threshold of the feature data such that the determination threshold is decreased as a value of the feature data of a pixel constituting the mucous-membrane area becomes more similar to a color property of the lesion area to be detected, and then create the criterion for the feature data based on the calculated determination threshold for the feature data.

Furthermore, in each embodiment described above, it is explained that the reddish lesion area is detected from the in-vivo images. However, the present invention is not limited to this example. As long as it is possible to determine in what color direction the color of the lesion area to be detected should deviate relative to the color of the mucous-membrane area, any methods can be employed in the same manner.

According to the present invention, it is possible to calculate feature data corresponding to a pixel or an area in the in-vivo image, and a pixel and an area whose feature data corresponds to a predetermined threshold can be extracted as a body tissue. Then, the criterion for detecting an object can be created based on the feature data of the body tissue, and a body tissue corresponding to the criterion can be detected as a detecting object. Therefore, it is possible to detect a detecting object such as a lesion area for example from the in-vivo image with good precision.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:
an image acquiring unit that acquires an in-vivo image being a captured image of an inside of a body cavity;
a processor; and
a memory storing computer readable instructions that, when executed by the processor, implement:
a feature-data calculating unit that calculates feature data corresponding to a pixel or an area in the in-vivo image;
a body-tissue extracting unit that extracts, as a body tissue, a pixel or an area whose feature data corresponds to a predetermined threshold;
a criterion creating unit that creates a criterion for detecting a detecting object based on the feature data of the body tissue;
a detecting unit that detects a body tissue corresponding to the criterion as the detecting object; and
a distribution forming unit that obtains a feature-data distribution of the body tissue based on the feature data, wherein the criterion creating unit creates the criterion based on the feature-data distribution of the body tissue and a known property of the feature data of the detecting object;
wherein the criterion is a determination threshold in a feature space, and the criterion creating unit sets a determination threshold at a location closer to a location of the feature-data distribution of the body tissue in the feature space as the location of the feature-data distribution of the body tissue comes closer to the known property of the feature data of the detecting object.

2. An image processing apparatus comprising:
an image acquiring unit that acquires a series of in-vivo images being sequentially-captured images of an inside of a body cavity;
a processor; and
a memory storing computer readable instructions that, when executed by the processor, implement:
an image extracting unit that extracts one or more in-vivo images from the series of in-vivo images;
a feature-data calculating unit that calculates feature data corresponding to a pixel or an area in the in-vivo images extracted by the image extracting unit;
a body-tissue extracting unit that extracts, as a body tissue, a pixel or an area whose feature data corresponds to a predetermined threshold from the in-vivo images extracted by the image extracting unit;
a criterion creating unit that creates a criterion for detecting a detecting object based on the feature data of the body tissue;
a detecting unit that detects a body tissue corresponding to the criterion as the detecting object; and
a distribution forming unit that obtains a feature-data distribution of the body tissue based on the feature data, wherein the criterion creating unit creates the criterion based on the feature-data distribution of the body tissue and a known property of the feature data of the detecting object;
wherein the criterion is a determination threshold in a feature space, and the criterion creating unit sets a determination threshold at a location closer to a location of the feature-data distribution of the body tissue in the feature space as the location of the feature-data distribution of the body tissue comes closer to the known property of the feature data of the detecting object.

3. The image processing apparatus according to claim 1, wherein the feature data is hue and saturation.

4. The image processing apparatus according to claim 3, wherein
the criterion creating unit sets the determination threshold in the saturation direction based on respective values of hue of the feature-data distribution of the body tissue.

5. The image processing apparatus according to claim 4, wherein
the criterion creating unit sets the determination threshold in the saturation direction so that the determination threshold in the saturation direction is decreased as the hue of the feature-data distribution of the body tissue comes closer to known hue of the detecting object.

6. The image processing apparatus according to claim 5, wherein
the criterion creating unit sets the determination threshold in the saturation direction according to a decreasing function represented by the following Equation (1) with the value of the hue of the feature-data distribution of the body tissue, $$T_S = (1/(H+1)) \times T_{h1} \qquad (1)$$

where $T_S$ is the determination threshold in the saturation direction, H is the value of the hue of the feature-data distribution of the body tissue, and $T_{h1}$ is a predetermined coefficient.

7. The image processing apparatus according to claim 3, wherein
the criterion creating unit sets the determination threshold in the saturation direction based on respective values of hue and saturation of the feature-data distribution of the body tissue.

8. The image processing apparatus according to claim 7, wherein
the criterion creating unit sets the determination threshold in the saturation direction so that the determination threshold in the saturation direction is decreased as the hue and the saturation of the feature-data distribution of the body tissue come closer to known hue and known saturation of the detecting object, respectively.

9. The image processing apparatus according to claim 8, wherein
the criterion creating unit sets the determination threshold in the saturation direction according to a decreasing function represented by the following Equation (2) with respective values of the hue and the saturation of the feature-data distribution of the body tissue, $$T_S = (1/(H+1)) \times T_{h1} - S \times T_{s1} \qquad (2)$$

where $T_S$ is the determination threshold in the saturation direction, H is the value of the hue of the feature-data distribution of the body tissue, S is the value of the saturation of the feature-data distribution of the body tissue, and $T_{h1}$ and $T_{s1}$ are predetermined coefficients.

10. The image processing apparatus according to claim 3, wherein
the criterion creating unit sets a determination threshold in a hue direction based on the value of the hue of the feature-data distribution of the body tissue.

11. The image processing apparatus according to claim 10, wherein
the criterion creating unit sets the determination threshold in the hue direction so that the determination threshold in the hue direction is decreased as the hue of the feature-data distribution of the body tissue comes closer to known hue of the detecting object.

12. The image processing apparatus according to claim 11, wherein
the criterion creating unit sets the determination threshold in the hue direction according to a decreasing function represented by the following Equation (3) with the value of the hue of the feature-data distribution of the body tissue, $$T_H = (1/(H+1)) \times T_{h2} \qquad (3)$$

where $T_H$ is the determination threshold in the hue direction, H is the value of the hue of the feature-data distribution of the body tissue, and $T_{h2}$ is a predetermined coefficient.

13. The image processing apparatus according to claim 3, wherein
the criterion creating unit sets the determination threshold in the hue direction based on respective values of hue and saturation of the feature-data distribution of the body tissue.

14. The image processing apparatus according to claim 13, wherein
the criterion creating unit sets the determination threshold in the hue direction so that the determination threshold is decreased as the hue and the saturation of the feature-data distribution of the body tissue come closer to known hue and known saturation of the detecting object, respectively.

15. The image processing apparatus according to claim 14, wherein
the criterion creating unit sets the determination threshold in the hue direction according to a decreasing function represented by the following Equation (4) with respective values of the hue and the saturation of the feature-data distribution of the body tissue, $$T_H = (1/(H+1)) \times T_{h2} - S \times T_{s2} \qquad (4)$$

where $T_H$ is the determination threshold in the hue direction, H is the value of hue of the feature-data distribution of the body tissue, S is the value of the saturation of the feature-data distribution of the body tissue, and $T_{h2}$ and $T_{s2}$ are predetermined coefficients.

16. An image processing method comprising:
acquiring an in-vivo image being a captured image of an inside of a body cavity;
calculating feature data corresponding to a pixel or an area in the in-vivo image;
extracting, as a body tissue, a pixel or an area whose feature data corresponds to a predetermined threshold;
creating a criterion for detecting a detecting object based on the feature data of the body tissue;
detecting a body tissue corresponding to the criterion as the detecting object; and
obtaining a feature-data distribution of the body tissue based on the feature data, wherein the criterion creating creates the criterion based on the feature-data distribution of the body tissue and a known property of the feature data of the detecting object;
wherein the criterion is a determination threshold in a feature space, and the criterion creating sets a determination threshold at a location closer to a location of the feature-data distribution of the body tissue in the feature space as the location of the feature-data distribution of the body tissue comes closer to the known property of the feature data of the detecting object.

17. A computer readable recording device having stored therein an image processing program including instructions, the instructions causing a computer to execute:
acquiring an in-vivo image being a captured image of an inside of a body cavity;
calculating feature data corresponding to a pixel or an area in the in-vivo image;
extracting, as a body tissue, a pixel or an area whose feature data corresponds to a predetermined threshold;
creating a criterion for detecting a detecting object based on the feature data of the body tissue;
detecting a body tissue corresponding to the criterion as the detecting object; and
obtaining a feature-data distribution of the body tissue based on the feature data, wherein the criterion creating creates the criterion based on the feature-data distribution of the body tissue and a known property of the feature data of the detecting object;
wherein the criterion is a determination threshold in a feature space, and the criterion creating sets a determination threshold at a location closer to a location of the feature-data distribution of the body tissue in the feature space as the location of the feature-data distribution of the body tissue comes closer to the known property of the feature data of the detecting object.

18. An image processing apparatus comprising:
an image acquiring unit that acquires an in-vivo image being a captured image of an inside of a body cavity;
a feature-data calculating unit that calculates feature data corresponding to a pixel or an area in the in-vivo image;
a body-tissue extracting unit that extracts, as a body tissue, a pixel or an area whose feature data corresponds to a predetermined threshold;
a criterion creating unit that creates a criterion for detecting a detecting object based on the feature data of the body tissue;
a detecting unit that detects a body tissue corresponding to the criterion as the detecting object; and
a distribution forming unit that obtains a feature-data distribution of the body tissue based on the feature data, wherein the criterion creating unit creates the criterion based on the feature-data distribution of the body tissue and a known property of the feature data of the detecting object;
wherein the criterion is a determination threshold in a feature space, and the criterion creating unit sets a determination threshold at a location closer to a location of the feature-data distribution of the body tissue in the feature space as the location of the feature-data distribution of the body tissue comes closer to the known property of the feature data of the detecting object.

19. An image processing apparatus comprising:
an image acquiring unit that acquires a series of in-vivo images being sequentially-captured images of an inside of a body cavity;
an image extracting unit that extracts one or more in-vivo images from the series of in-vivo images;
a feature-data calculating unit that calculates feature data corresponding to a pixel or an area in the in-vivo images extracted by the image extracting unit;
a body-tissue extracting unit that extracts, as a body tissue, a pixel or an area whose feature data corresponds to a predetermined threshold from the in-vivo images extracted by the image extracting unit;
a criterion creating unit that creates a criterion for detecting a detecting object based on the feature data of the body tissue;
a detecting unit that detects a body tissue corresponding to the criterion as the detecting object; and a distribution forming unit that obtains a feature-data distribution of the body tissue based on the feature data, wherein the criterion creating unit creates the criterion based on the feature-data distribution of the body tissue and a known property of the feature data of the detecting object;

wherein the criterion is a determination threshold in a feature space, and the criterion creating unit sets a determination threshold at a location closer to a location of the feature-data distribution of the body tissue in the feature space as the location of the feature-data distribution of the body tissue comes closer to the known property of the feature data of the detecting object.

* * * * *